United States Patent [19]

Martin et al.

[11] 4,414,219

[45] Nov. 8, 1983

[54] ANTIDEPRESSANT (α-PHENYL-2-TOLYL)AZACYCLOALKANOLS AND DERIVATIVES THEREOF

[75] Inventors: Lawrence L. Martin, Lebanon; Helen H. Ong, Whippany; Vernon B. Anderson, High Bridge; Charles A. Crichlow, Piscataway, all of N.J.

[73] Assignee: American Hoechst Corporation, Somerville, N.J.

[21] Appl. No.: 174,435

[22] Filed: Aug. 1, 1980

Related U.S. Application Data

[60] Division of Ser. No. 6,791, Jan. 25, 1979, Pat. No. 4,241,071, which is a continuation-in-part of Ser. No. 763,294, Jan. 27, 1977, abandoned.

[51] Int. Cl.$^3$ .................. A61K 31/445; A61K 31/40; C07D 211/52; C07D 211/42
[52] U.S. Cl. .................................... 424/267; 424/274; 546/216; 546/217; 546/218; 546/222; 548/541; 548/556
[58] Field of Search ............... 546/218, 222, 216, 217; 260/326.47, 326.5 M, 326.5 R; 424/267, 274; 548/541, 556

[56] References Cited

U.S. PATENT DOCUMENTS

| 2,975,185 | 3/1961 | Anderson et al. | 546/217 |
| 3,301,862 | 1/1967 | Biel et al. | 546/217 X |
| 3,350,403 | 10/1967 | Biel et al. | 546/217 |
| 3,674,806 | 7/1972 | Bluhm et al. | 424/263 X |

OTHER PUBLICATIONS

Martin, L., et al., *J. Med. Chem.*, 22,1347 (1979).
Kaiser, C., et al., *J. Med. Chem.*, 25,697 (1982).

*Primary Examiner*—Richard A. Schwartz
*Attorney, Agent, or Firm*—Curtis, Morris & Safford

[57] ABSTRACT

Novel azacycloalkanes, azacycloalkenes and derivatives thereof and methods of preparing same are described. These compounds are useful as antidepressants, anticonvulsants, tranquilizers and analgetics.

50 Claims, No Drawings

ANTIDEPRESSANT (α-PHENYL-2-TOLYL)AZACYCLOALKANOLS AND DERIVATIVES THEREOF

This is a division of application Ser. No. 006,791 now U.S. Pat. No. 4,241,071 filed Jan. 25, 1979 which is a continuation in part of Ser. No. 763,294 filed Jan. 27, 1977 (abandoned).

This invention relates to novel azacycloalkanes, azacycloalkenes and derivatives thereof which are useful as antidepressants, anticonvulsants, tranquilizers, analgetics and as intermediates therefor, to methods of preparing the same, to methods of treatment with pharmaceutically effective amounts thereof, and to pharmaceutical compositions containing such compounds as essential active ingredients.

To the best of our knowledge, the compounds of this invention have not heretofore been made, used, described or suggested.

Bauer et al., in U.S. Pat. No. 3,959,475, describe substituted 1,3-dihydrospiro(isobenzofuran)s of the formula

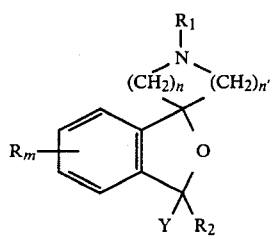

in which R is hydrogen, alkyl of 1 to 6 carbon atoms, alkoxy of 1 to 6 carbon atoms, trifluoromethyl, halogen, hydroxy, or methylenedioxy; $R_1$ is hydrogen, alkyl of 1 to 6 carbon atoms, cycloalkylalkyl of 4 to 8 carbon atoms, alkenyl of 3 to 6 carbon atoms, phenylalkyl of the formula $-(CH_2)_x-PhR$, diphenylalkyl of the formula $-(CH_2)_m-CH(PhR)_2$, diphenylmethoxyalkyl of the formula $-(CH_2)_m-OCHPh_2$, alkanoyl of 2 to 6 carbon atoms, phenylalkanoyl of the formula $-CO(CH_2)_x-PhR$, benzoyl of the formula $-COPhR$, benzoylalkyl of the formula $-(CH_2)_m-COPhR$, phenylhydroxyalkyl of the formula $-(CH_2)_mCHOHPhR$, alkoxycarbonyl of 2 to 6 carbon atoms, phenyloxycarbonyl or cycloalkylcarbonyl of 4 to 8 carbon atoms; $R_2$ is alkyl of 1 to 6 carbon atoms or phenyl of the formula $-PhR_m$; Y is hydrogen, alkyl of 1 to 6 carbon atoms, alkoxy of 1 to 6 carbon atoms, hydroxy or phenyl of the formula PhR; Ph is phenyl; m, n and n' are integers from 1 to 3; and x is an integer from 1 to 4, as well as the optical antipodes and the pharmaceutically acceptable acid addition salts thereof. Additionally, the same patent describes, as intermediates, o-hydroxyalkylphenylcycloazalkanols of the formula

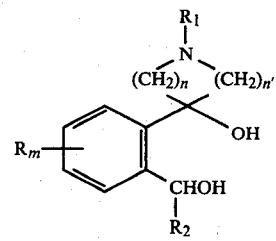

and o-hydroxyalkylphenylcycloazalkanols or their ethers of the formula

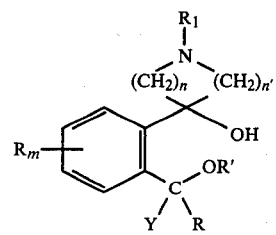

in which R' is hydrogen, alkyl or tetrahydropyranyl. These intermediate compounds were not found to demonstrate any biological activity.

Bauer et al., in U.S. Pat. No. 3,962,259 describe, also as intermediates, o-hydroxymethylphenylcycloazalkanols and their ethers of the formula

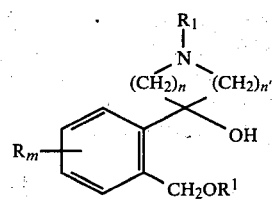

wherein $R^1$ is hydrogen or alkyl, R and $R_1$, m, n and n' are as defined earlier. These intermediates do not structurally suggest the instantly described compounds and were not found to demonstrat biological activity.

Biel et al., in U.S. Pat. Nos. 3,301,862 and 3,350,403, refer generically to intermediate compounds of the formula

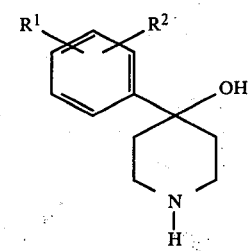

wherein either or both $R^1$ and $R^2$ can be benzyl. This, as will be seen below, is pertinent because compounds described in the present application are technically within the scope of this broad generic disclosure. However, the Biel et al. patents neither suggest nor describe a single compound in which a benzyl group is substituted in the 2- or ortho position of the phenyl ring, the only benzyl-containing intermediate specifically identified being 4-(3-benzylphenyl)-4-hydroxypiperidine. We have found the substitution of a benzyl in this 2- or ortho position to bear a critical relationship to biological, especially antidepressant activity. Additionally, there is no teaching of how to make the aforesaid intermediate compounds and no actual disclosure of a compound within the aforementioned generic formula wherein the benzyl group is on this 2- or ortho position.

Similarly, Biel et al., in U.S. Pat. Nos. 3,221,017 and 3,221,018, refer generically to 1,2,5,6-tetrahydropyridines of the formula

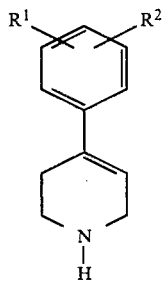

wherein benzyl is included within the definition of $R^1$ and $R^2$, as intermediates in the preparation of 4-arylpyridines. These patents, like the aforementioned U.S. Pat. Nos. 3,301,862 and 3,350,403, also neither suggest nor disclose a single compound within the scope of the present application, the only such intermediate identified in these patents being the 3-benzyl-substituted compound, 4-(3-benzylphenyl)-1,2,5,6-tetrahydropyridine. Neither Beil et al. patent discloses or suggests any biological activity for these intermediates.

It is apparent from the disclosure in the Biel et al. patents, e.g., lines 14 to 18, column 5 of U.S. Pat. No. 3,221,018, that the starting materials used in the processes of Biel et al. are compounds which are either commercially available, well known in the art or easily prepared and do not apply to any of the compounds, including the position isomers, disclosed and claimed in this application.

This invention relates to azacycloalkanes, azacycloalkenes and derivates thereof of the formula

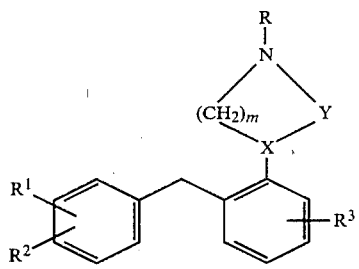

wherein X is C—$R^4$ or C; Y is —(CH$_2$)$_n$— when X is CR$^4$ and =CH—CH$_2$— or —CH=CH— when X is C; R is hydrogen, loweralkyl, phenylloweralkyl of the formula

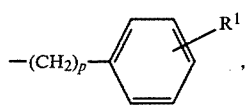

hydroxy, benzoylloweralkyl of the formula $$-(CH_2)_p-\overset{\overset{\displaystyle O}{\|}}{C}-\bigcirc\!\!\!\!\!\!-R^1 ,$$

cycloalkylloweralkyl in which the cycloalkyl ring contains from 3–6 carbon atoms, alkoxy carbonyl of from 2 to 6 carbon atoms, phenyloxycarbonyl, benzoyl, benzoyloxy, $$-(CH_2)_p-\overset{\overset{\displaystyle O \diagup \diagdown O}{|\quad |}}{C}-\bigcirc\!\!\!\!\!\!-R^1 ,$$

formal or 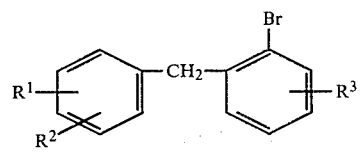

$R^1$, $R^2$ and $R^3$ are the same or different and each can be hydrogen, halogen, alkoxy of 1 or 2 carbon atoms, loweralkyl, hydroxy or trifluoromethyl; $R^4$ is hydrogen or OR$^5$; $R^5$ is hydrogen, loweralkyl, loweracyl, benzoyl or lowercycloacyl; m is the integer 1 or 2; n is the integer 1, 2 or 3; the sum of m and n is 3 or 4; p is the integer 1, 2, 3 or 4; and the pharmaceutically acceptable acid addition salts thereof. In the above, the term "lower" means the radical described contains from 1 to 5 carbon atoms.

Compounds which are preferred due to their biological activity are those wherein R is hydrogen, alkyl or hydroxy. Most preferred compounds within this group are those wherein X is C—H.

Acids useful for preparing the pharmaceutically acceptable acid addition salts of the invention include inorganic acids such as hydrochloric, hydrobromic, sulfuric, nitric, phosphoric and perchloric acids, as well as organic acids such as tartaric, citric, acetic, succinic, maleic, fumaric and oxalic acids.

Some compounds within the scope of this invention have greater pharmaceutical activity than others. The latter are nevertheless desirable as intermediates for the preparation of the more active compounds, as will become apparent from the following description of several methods of preparation.

Method A

A 2-bromodiphenylmethane of the formula in which $R^1$, $R^2$ and $R^3$, with the exclusion of hydroxy, are as defined above, is converted to its lithio derivative by treatment with an alkyllithium at reduced temperature of about −80° to −30° C. in a solvent such as ether, hexane or tetrahydrofuran. The resulting lithio derivative is allowed to react with a compound of the formula

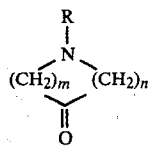

wherein m and n and the sum of m and n being as defined above and R is loweralkyl, phenylloweralkyl or cycloalkylloweralkyl, at a temperature of −80° to −20° C., preferably −60° to −30° C., in a solvent such as ether, tetrahydrofuran or hexane to provide the corresponding N-substituted azacycloalkanol, a compound of the invention of the formula.

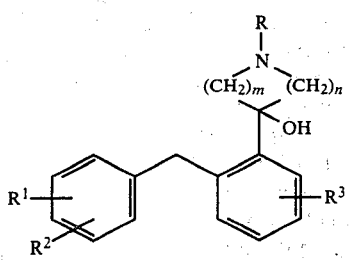

The starting 2-bromodiphenylmethane is prepared by reducing a corresponding 2-bromobenzophenone. One suitable method of carrying out this reduction is via the Clemmensen reduction. Another very suitable method involves the use of hydroiodic acid and phosphorus under reflux conditions. One suitable method of preparing a 2-bromobenzophenone is by reacting a 2-bromobenzoyl chloride of the formula

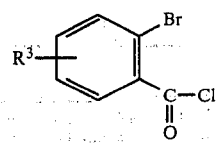

with a benzene of the formula

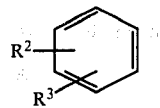

under Friedel-Crafts conditions.

Method B

An above N-substituted azacycloalkanol, described in Method A, wherein R is benzyl, can by hydrogenated, e.g., with a palladium on carbon catalyst to provide an N-unsubstituted azacycloalkanol.

Method C

An N-substituted azacycloalkanol, described in Method A, can be esterified by treatment with an appropriate acid anhydride, acid or acid chloride to provide an ester of the invention wherein X is C—OR$^5$ and R$^5$ is loweracyl, benzoyl or lowercycloalkyl. In some instances yields may be enhanced by converting the azacycloalkanol to its lithio derivative which is in turn exterified.

Method D

An N-unsubstituted azacycloalkanol, described in Method B can be reacted in a known manner with benzoyl chloride to provide the corresponding N-benzoyl azacycloalkanol.

Method E

An azacycloalkanol, described in Methods A or B is dehydrated to its corresponding azacycloalkene of the formula

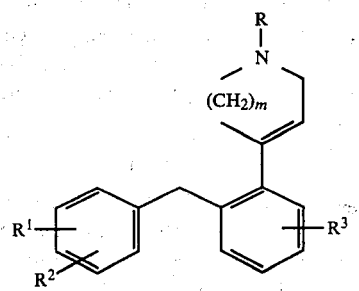

The dehydration can be carried out with one of several dehydrating agents including trifluoroacetic acid, formic acid and a mixture of glacial acetic and concentrated hydrochloric acids and from ambient to the reflux temperature of the reaction mixture.

Method F

An azacycloalkene prepared according to Method E can be hydrogenated as described in Method B to prepare the corresponding N-unsubstituted or substituted azacycloalkane, a compound of the invention of the formula

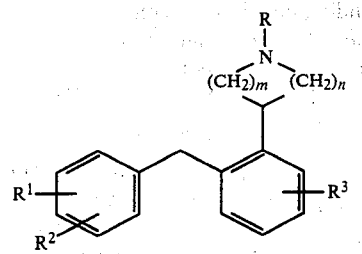

wherein R≠benzyl.

Method G

As N-substituted cycloazalkane, prepared according to Method F, wherein R is alkyl can be treated with a chloroformate, e.g. an alkyl or phenyl chloroformate, at a temperature of from 25° to 125° C., in a solvent such as toluene, benzene or methylene chloride to provide the corresponding N-alkoxycarbonyl or N-phenyloxycarbonylcycloazalkane, a compound of the invention.

Method H

An N-alkoxycarbonyl or N-phenyloxycarbonylcycloazalkane, prepared in Method G, is treated with a base such as sodium or potassium hydroxide in a solvent such as water or ethanol or with an acid such as hydrogen bromide in acetic acid at a temperature of from ambient to 125° C. to provide the corresponding N-unsubstituted azacycloalkane, a compound of the invention.

Method I

An N-unsubstituted compound, prepared by Method B, C, E, F or H, can be converted to the corresponding N-benzoyloxy compound, a compound of the invention, by the addition of a cooled solution of benzoyl peroxide in a suitable organic solvent such as benzene.

Method J

An N-benzoyloxy compound, prepared in Method I, is converted to its corresponding N-hydroxy compound, a compound of the invention, by a method known to the art. One such method is the cleaving of the benzoyloxy group by the treatment with aqueous potassium or sodium hydroxide in ethanol and permitting the mixture to react at the reflux temperature of the reaction mixture.

Method K

An ester, prepared by Method C, can be hydrogenated all the way to its corresponding azacycloalkane by a method known to the art. One such method involves using a palladium on carbon catalyst.

Method L

An N-unsubstituted compound, prepared by Method B, C, E, F or H can be reacted with a compound of the formula

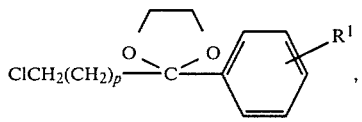

wherein p and $R^1$ are as defined earlier, to produce a corresponding compound. This reaction can be carried out in the presence of an organic solvent such as n-butanol and an acid scavenger at ambient temperature to the reflux point of the reaction mixture.

Method M

A compound prepared in Method L can be subjected to hydrolysis by a method known to the art to provide an N-benzoylalkyl compound, a compound of the invention. One such method is carried out with a refluxing mixture of methanol and concentrated hydrochloric acid.

Method N

An alkoxy containing compound, wherein an alkoxy group is situated on a phenyl ring, can be dealkylated by a method known to the art to provide a corresponding phenolic compound. A preferred method is dealkylating with refluxing hydrobromic acid, under an inert atmosphere such as nitrogen.

The compounds of the invention are useful in the treatment of depression in mammals, as demonstrated by their ability to inhibit tetrabenazine-induced ptosis in mice [International Journal of Neuropharmacology, 8, 73 (1969)], a standard assay useful for evaluating antidepressant properties. Thus, for instance, the intraperitoneal dosages at which the following compounds ($ED_{50}$) effect a 50% inhibition from the ptosis of tetrabenazine-induced depression in mice are:

TABLE I

| | $ED_{50}$ Mg/Kg |
|---|---|
| 4-(α-phenyl-2-tolyl)piperidine hydrochloride | 1.7 |
| 4-(α-phenyl-2-tolyl)-1,2,3,6-tetrahydropyridine | 2.1 |
| 1-methyl-4-(α-phenyl-2-tolyl)piperidine hydrochloride | 2.5 |
| 4-(α-phenyl-2-tolyl)-4-piperidinol hydrochloride | 5.4 |
| 4-[α-(4-fluorophenyl)-2-tolyl]-1-methyl-1,2,3,6-tetrahydropyridine hydrobromide | 8.0 |
| 4-[α-(4-fluorophenyl)-2-tolyl]-1-methyl-4-piperidinol | 8.2 |
| 1-methyl-4-(α-phenyl-2-tolyl)-1,2,3,6-tetrahydropyridine | 8.8 |
| 1-methyl-4-(α-phenyl-2-tolyl)-4-piperidinol | 8.0 |
| 1-hydroxy-4-(α-phenyl-2-tolyl)piperidine | 3.0 |

Similarly a 25 mg/kg intraperitoneal dosage of 4-acetoxy-1-methyl-4-(α-phenyl-2-tolyl)piperidine hydrochloride effects a 40% inhibition from the ptosis of tetrabenazine-induced depression. These data illustrate that compounds of the invention are useful in the treatment of depression when administered in amounts ranging from 0.1 and 50 mg/kg.

It is to be noted and stressed at this point that the substitution of a benzyl in the 2- or ortho position of the phenyl ring, in the compounds of the invention, is critical to biological especially antidepressant, activity. Where the benzyl is substituted in the 3- or meta position or the 4- or para position, the corresponding compound is relatively ineffective as compared to the 2-substituted compounds of the invention. In this regard, reference is made to the following Table II which illustrates such criticality in the form of intraperitoneal dosages at which a series (A. B. and C.) of 2-, 3- and 4-substituted compounds effect a 50% inhibition from the ptosis of tetrabenazine-induced depression in mice:

TABLE II

| | | $ED_{50}$ mg/kg |
|---|---|---|
| A. | 4-(α-phenyl-2-tolyl)piperidine hydrochloride | 1.7 |
| | 4-(α-phenyl-3-tolyl)piperidine hydrochloride | >20 |
| | 4-(α-phenyl-4-tolyl)piperidine hydrochloride | >20 |
| B. | 1-methyl-4-(α-phenyl-2-tolyl)piperidine hydrochloride | 2.5 |
| | 1-methyl-4-(α-phenyl-3-tolyl)piperidine oxalate | >20 |
| | 1-methyl-4-(α-phenyl-4-tolyl)piperidine oxalate | >20 |
| C. | 1-methyl-4-(α-phenyl-2-tolyl)-1,2,3,6-tetrahydropyridine | 8.8 |
| | 1-methyl-4-(α-phenyl-3-tolyl)-1,2,3,6-tetrahydropyridine | >50 |
| | 1-methyl-4-(α-phenyl-4-tolyl)-1,2,3,6-tetrahydropyridine | >50 |

Compounds of the invention are also useful as analgesic agents due to their ability to alleviate pain in mammals. The analgesic utility of compounds of this invention is demonstrated in the 2-phenyl-1,4-quinone induced writhing assay in mice, a standard assay for analgesia [Proc. Soc. Exptl. Biol. Med., 95, 729 (1957)]. Thus, for example, a 50% inhibition in writhing is effected by the oral administration of 28.4 mg/kg of body weight of 4-acetoxy-1-methyl-4-(α-phenyl)-2-tolyl)-piperidine hydrochloride. Other representative compounds of the invention and their respective ability to inhibit said writhing is shown below in Table III.

TABLE III

| | Dose in mg/kg | % Inhibition in Writhing |
|---|---|---|
| 1-methyl-4-(α-phenyl-2-tolyl)-4-piperidinol | 50.0 po* | 41 |
| 1-methyl-4-(α-phenyl-2-tolyl)-piperidine hydrochloride | 61.7 po | 50 |
| 4-(α-phenyl-2-tolyl)-1,2,3,6-tetrahydropyridine | 7.8 sc** | 50 |
| 1-methyl-4-(α-phenyl-2-tolyl)-4-propionyloxypiperidine hydrochloride | 8.9 sc | 50 |
| 4-benzoyloxy-1-methyl-4-(α-phenyl-2-tolyl)piperidine hydrochloride | 12.8 sc | 50 |

*po means oral administration
**sc means subcutaneous administration

These data show that the compounds of the invention are useful as analgesic agents at a dose of 0.1 to 50 mg/kg of body weight. For comparison, aspirin and propoxyphene hydrochloride, known analgesic agents, effect a 34% and 50% inhibition of writhing, respectively, at a dose of 60 mg/kg p.o.

Compounds of the present invention are further useful as anticonvulsant agents for mammals, as determined by the method of Woodbury, L. A. and Davenport, V. D., in Arch, Int. Pharmacodynam, Vol. 92, (1952) at pages 97–107. For example, the intraperitoneal dose of 17.6 mg/kg of body weight of 1-methyl-4-[-(4,fluorophenyl)-2-tolyl]-1,2,3,6-tetrahydropyridine hydrobromide produces an 83% protection from the effect of supra maximal electro shock (SES). Intraperitoneal doses of other representative compounds of the invention and their ability to protect from the effect of SES is shown below in Table IV.

TABLE IV

| Compound | Dose mg/kg | % SES Protection |
|---|---|---|
| 1-benzyl-3-(α-phenyl-2-tolyl)-3-pyrrolidinol hydrochloride | 50 | 83 |
| 1-methyl-4-(α-phenyl-2-tolyl)-piperidine hydrochloride | 50 | 83 |
| 1-methyl-4-[α-(4-fluorophenyl)-2-tolyl]-4-piperidinol | 23.3 | 50 |
| 1-methyl-4-[α-(4-methoxyphenyl)-2-tolyl]-1,2,3,6-tetrahydropyridine hydrobromide | 25.6 | 50 |
| 1-methyl-4-(α-phenyl-2-tolyl)-4-piperidinol | 36 | 50 |
| 1-phenethyl-4-(α-phenyl-2-tolyl)-piperidine hydrobromide | 37.5 | 50 |
| 1-methyl-4-(α-phenyl-2-tolyl)-4-propionyloxypiperidine hydrochloride | 50 | 50 |

This data illustrates the utility of compounds of the invention for treatment of convulsion in mammals when administered in amounts ranging from about 1 to 50 mg/kg of body weight per day.

Compounds of the invention are still further useful as tranquilizers due to their ability to reverse toxicity of amphetamine as measured in the Amphetamine Aggregation Toxicity Reversal Assay [Chance, M. R. A., J. Pharmacol. Exper. Therap. 87, pp. 214–219 (1946) and Proctor, C. D., Putts, J. T., Lundy, R. O., and Greenfield, E. J., Arch. Int. Pharmacodynam. 163, (1), pp. 79–86 (1966)]. In our assay "aggregated mice" mean 5 mice/group placed in such a manner as to yield 20 cm² of floor space per mouse. Animals are aggregated immediately after injection with amphetamine sulfate and then checked for survival up to 3 hours. For example, under these conditions an oral dosage of 20 mg/kg of body weight of 1-[3-(4-fluorobenzoyl)propyl]-4-(α-phenyl-2-tolyl)piperidine effects a 60% protection against the intraperitoneal dose of 15 mg/kg of amphetamine sulfate. This data illustrates that compounds of the invention are useful as tranquilizers when administered in amounts ranging from 0.1 to 50 mg/kg.

Effective quantities of the compounds of the invention may be administered to a patient by any one of various methods, for example, orally as in capsules or tablets, parenterally in the form of sterile solutions or suspensions, and in some cases intravenously in the form of sterile solutions. The free base final products, while effective themselves, may be formulated and administered in the form of their pharmaceutically acceptable addition salts for purposes of stability, convenience of crystallization, increased solubility and the like.

The active compounds of the present invention may be orally administered, for example, with an inert diluent or with an edible carrier, or they may be enclosed in gelatin capsules, or they may be compressed into tablets. For the purpose of oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compound, but may be varied depending upon the particular form and may conveniently be between 4% to about 70% of the weight of the unit. The amount of active compound in such compositions is such that a suitable dosage will be obtained. Preferred compositions and preparations according to the present invention are prepared so that an oral dosage unit form contains between 1.0–300 milligrams of active compound.

The tablets, pills, capsules, troches, and the like may also contain the following ingredients: a binder such as microcrystalline cellulose, gum traugacanth or gelatin; an excipient such as starch or lactose, a disintegrating agent such as alginic acid, Primogel, corn starch and the like; a lubricant such as magnesium stearate or Sterotex; a glidant such as colloidal silicon dioxide; and a sweetening agent such as sucrose or saccharin may be added or a flavoring agent such as peppermint, methyl salicylate, or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active compounds, sucrose as a sweetening agent, and certain preservatives, dyes and colorings, and flavors. Materials used in preparing these various compositions should be pharmaceutically pure and non-toxic in the amounts used.

For the purpose of parenteral therapeutics administration, the active compounds of the invention may be incorporated into a solution or suspension. These preparations should contain at least 0.1% of active compound, but may be varied to be between 0.5 and about 50% of the weight thereof. The amount of active compounds in such compositions is such that a suitable dosage will be obtained. Preferred compositions and preparations according to the present invention are prepared so that a parenteral dosage unit contains between 0.5 to 100 milligrams of active compound.

The solutions or suspensions may also incude the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylene diaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

This invention is illustrated by the following examples:

1-methyl-4-(α-phenyl-3-trifluoromethyl-2-tolyl)-4-piperidinol;
1-n-butyl-4-(4-chloro-α-phenyl-2-tolyl)-3-pyrrolidinol;
4-(4-hydroxy-α-phenyl-2-tolyl)-1,2,3,6-tetrahydropyridine;
3-acetoxy-1-(3-phenylpropyl)-3-(4-ethoxy-α-phenyl-2-tolyl)pyrrolidine;
1-(3-phenethyl)-4-(α-phenyl-2-tolyl)-1,2,3,6-tetrahydropyridine; and
4-(4-t-butyl-α-phenyl-2-tolyl)-1-phenoxycarbonyl-piperidine.

This invention is further illustrated by the following examples and their preparation.

EXAMPLE 1

To a stirring solution at −40° C. of 18.5 g of 2-bromodiphenylmethane, 70 ml of tetrahydrofuran and 18 ml of anhydrous hexanes is added over a 20 minute span 38 ml of a 2.2 M solution of n-butyllithium in hexane. After total addition stirring is continued for 50 minutes after which time 8.84 g of 1-methyl-4-piperidone in 25 ml of tetrahydrofuran is added with stirring over a 25 minute span while maintaining this low temperature. After total addition the solution is permitted to stir at this same temperature for 1.5 hours and then warmed to 0° C. The reaction solution is hydrolyzed with 25 ml of water with ice-water cooling. The resulting suspension is diluted by the addition of 200 ml of water and 500 ml of hexanes. The suspension is shaken vigorously, the aqueous phase separated and the organic phase washed with 200 ml of water. The organic phase is suction filtered and the filter cake washed well with hexane and dried. Recrystallization of the dried filter cake from toluene leaves colorless crystals, mp 163°–165° C., of 1-methyl-4-(α-phenyl-2-tolyl)-4-piperidinol.

Analysis: Calculated for $C_{19}H_{23}NO$: 81.08%C; 8.25%H; 4.98%N. Found: 80.91%C; 8.10%H; 4.90%N.

EXAMPLES 2–6

By following the manipulative procedure outlined above in Example 1 the reaction of 2-bromo-4′-methoxydiphenylmethane and 1-methyl-4-piperidone; 2-bromo-4′-fluorodiphenylmethane and 1-methyl-4-piperidone; 2-bromo-2′-fluoro-4′-methyldiphenylmethane and 1-methyl-4-piperidone; 2-bromodiphenylmethane and 1-(2-phenethyl)-4-piperidone; and 2′-bromo-2,5-difluorodiphenylmethane and 1-methyl-4-piperidone provides 1-methyl-4-[α-(4-methoxyphenyl)-2-tolyl]-4-piperidinol, 1-methyl-4-[α-(4-fluorophenyl)-2-tolyl]-4-piperidinol, 1-methyl-4-[α-(2-fluoro-4-methylphenyl)-2-tolyl]-4-piperidinol, 1-(2-phenethyl)-4-(α-phenyl-2-tolyl)-4-piperidinol, and 1-methyl-4-[α-(2,5-difluorophenyl)-2-tolyl]-4-piperidinol, respectively, as listed in Table 1 sequentially as Examples 2–6.

TABLE 1

| Ex. | Recryst'n Solvent | m.p. °C. | Empirical Formula | Analysis Calculated | | | Analysis Found | | |
|---|---|---|---|---|---|---|---|---|---|
| | | | | % C | % H | % N | % C | % H | % N |
| 2 | isoprop. | 142–144 | $C_{20}H_{25}NO_2$ | 77.14 | 8.09 | 4.28 | 76.86 | 8.15 | 4.48 |
| 3 | hexane | 142–144 | $C_{19}H_{22}FNO$ | 76.22 | 7.41 | 4.68 | 76.14 | 7.44 | 4.71 |
| 4 | benzene-hexane | 157–159 | $C_{20}H_{24}FNO$ | 76.64 | 7.68 | 4.47 | 76.62 | 7.84 | 4.45 |
| 5 | toluene | 135–138 | $C_{26}H_{29}NO$ | 84.04 | 7.88 | 3.77 | 84.14 | 8.05 | 3.71 |
| 6 | acetone-hexane | 150–152 | $C_{19}H_{21}F_2NO$ | 71.89 | 6.67 | 4.41 | 71.72 | 6.80 | 4.47 |

EXAMPLE 7

To a solution of 5.0 g of 2-bromo-2′-fluoro-4′-methyldiphenylmethane in 50 ml of tetrahydrofuran at −60° C. is added dropwise 9 ml 2.4 M of n-butyllithium. After total addition the solution is stirred for 30 minutes and then a solution of 3.41 g of 1-benzyl-4-piperidone in 10 ml of tetrahydrofuran is added dropwise while maintaining the reaction temperature at −60° C. The reaction mixture is kept at this temperature for 30 minutes and then poured into 400 ml of ice cooled water. The resulting mixture is extracted with ether and the ether extract dried, concentrated and the hydrochloride salt prepared. The salt is collected by filtration and dissolved in chloroform. The chloroform solution is washed with water, dried, filtered and the chloroform evaporated off leaving a white solid. The solid is recrystallized from a methanol-acetone-ether mixture to leave the salt mp 216°–218° C., of 1-benzyl-4-[α-(2-fluoro-4-methylphenyl)-2-tolyl]-4-piperidinol hydrochloride.

Analysis: Calculated for $C_{26}H_{28}FNO \cdot HCl$: 73.31%C; 6.86%H; 3.29%H. Found: 73.12%C; 6.93%H; 3.06%H.

EXAMPLE 8

To a solution of 5.6 g of 2′-bromo-2,5-difluorodiphenylmethane in 18 ml of tetrahydrofuran at −50° C. is added dropwise 14 ml of n-butyllithium while maintaining the temperature below −50° C. After total addition the reaction mixture is stirred at a temperature of from −60° to −70° C. for 30 minutes. A solution of 3.5 g of 1-benzyl-3-pyrrolidone in 5 ml of tetrahydrofuran is added dropwise, the reaction mixture is stirred at this temperature for 30 minutes, after which time ice is added and the resulting mixture extracted twice with 200 ml portions of ether. The combined ether extracts are shaken with 120 ml of 1 N hydrochloric acid which produces an oily residue. The ether and aqueous layers are carefully discarded and the oily residue is basified with dilute ammonium hydroxide. The basic solution is extracted with ether and the ether extract dried. The ether solution is treated with ethereal hydrogen bromide to produce a crystalline salt which is recrystallized from a methanol-ether mixture to provide the crystals mp 203°–205° C., of 1-benzyl-3-[α-(2,5-difluorophenyl)-2-tolyl]-3-pyrrolidinol hydrobromide.

Analysis: Calculated for $C_{24}H_{23}F_2NO \cdot HBr$: 62.59%C; 5.25%H; 3.04%N. Found: 62.51%C; 5.39%H; 3.05%N.

EXAMPLE 9

By following the procedure outlined above in Example 8, substituting 1-benzyl-4-piperidone for 1-benzyl-3-pyrrolidone, produces 1-benzyl-4-[α-(2,5-difluorophenyl)-2-tolyl]-4-piperidinol.hydrobromide, mp 143°–146° C.

Analysis: Calculated for $C_{25}H_{25}F_2NO \cdot HBr$: 63.30%C; 5.52%H; 2.95%N; 16.84%Br. Found: 63.28%C; 5.64%H; 3.01%N; 16.82%Br.

EXAMPLE 10

To a solution at −50° C. of 5.6 g of 2-bromo-2'-fluoro-4'-methyldiphenylmethane in 15 ml of tetrahydrofuran is added dropwise 11 ml of 2.2 M butyllithium while maintaining the reaction temperature below −50° C. After total addition stirring is continued at −60° to −70° C. for 30 minutes and then a solution of 3.5 g of 1-benzyl-3-pyrrolidone in 5 ml of tetrahydrofuran is added over a 5 minute span. After total addition stirring is continued at this low temperature for 30 minutes, ice added, and then the organic material extracted twice with 200 ml portions of ether. The combined ether extracts are shaken vigorously with an excess of 1 N hydrochloric acid which produces an oily residue which solidifies slowly upon standing. The solid is recrystallized from a methanol-acetone-ether mixture to give off-white prisms, mp 292°–294° C., of 1-benzyl-3-[α-(2-fluoro-4-methylphenyl)-2-tolyl]-3-pyrrolidinolhydrochloride.

Analysis: Calculated for $C_{25}H_{26}FNO \cdot HCl$: 72.90%C; 6.60%H; 3.40%N; 8.60%Cl. Found: 72.64%C; 6.77%H; 3.35%N; 8.44%Cl.

EXAMPLE 11

By following the manipulative procedure outlined above in Example 10, substituting 1-(2-phenethyl)-4-piperidone for 1-benzyl-3-pyrrolidone produces the white powder, 262°–263° C., of 4-[α-(2-fluoro-4-methylphenyl)-2-tolyl]-1-phenethyl-4-piperidinol hydrochloride.

Analysis: Calculated for $C_{27}H_{30}FNO \cdot HCl$: 73.70%C; 7.10%H; 3.18%N; 8.06%Cl. Found: 73.49%C; 7.21%H; 3.00%N; 8.15%Cl.

EXAMPLE 12

To a stirring solution at −50° C. of 18.5 g of 2-bromo diphenylmethane, 70 ml of tetrahydrofuran and 18 ml of hexane is added over a 30 minute span a 40 ml of 2.2 M hexane solution of n-butyllithium. After total addition the solution is stirred at −50° C. for 30 minutes and then a solution of 14.8 g of 1-benzyl-4-piperidone in 40 ml of tetrahydrofuran is added over a 30 minute span. After total addition the solution is stirred at −50° C. for 60 minutes, permitted to warm to −30° C., and then quenched with 40 ml of water. The reaction mixture is diluted with 400 ml of water and 500 ml of hexane. The organic and aqueous phases separated and the organic phase collected and washed with water. The washed organic phase is evaporated leaving an oil which is azeotropically dried with benzene. The oil is diluted with equal volume of hexane and the hexane mixture chilled at 5° C. for 2 hours. The upper phase is decanted and the hexane washing procedure is repeated twice. The ultimate lower phase is diluted in 50 ml of tetrahydrofuran, acidified with a 5% hydrochloric acid solution causing a dark oil to separate as the upper phase. The biphasic mixture is extracted thrice with 75 ml portions of chloroform and the combined extracts are washed with water and then a 5% sodium hydroxide solution. The organic solution is dried, filtered and the filtrate evaporated to an oil which is dissolved in ether and precipitated as a hydrogen chloride salt. The salt is dried in vacuo at ambient temperature and then recrystallized from acetonitrile leaving slightly tan colored crystals, mp 190°–191° C., of 1-benzyl-4-(α-phenyl-2-tolyl)-4-piperidinol hydrochloride.

Analysis: Calculated for $C_{25}H_{27}NO \cdot HCl$: 76.21%C; 7.18%H; 3.56%N; 9.00%Cl. Found: 76.22%C; 7.24%H; 3.47%N; 8.82%Cl.

EXAMPLE 13

By following the manipulative procedure outlined above in Example 12, substituting 1-benzyl-3-pyrrolidone for 1-benzyl-4-piperidone, produces 1-benzyl-3-(α-phenyl-2-tolyl)-3-pyrrolidinol hydrochloride.

Analysis: Calculated for $C_{24}H_{25}NO \cdot HCl$: 75.86%C; 6.91%H; 3.69%N; 9.33%Cl. Found: 75.62%C; 6.96%H; 3.69%N; 9.15%Cl.

EXAMPLE 14

To a 500 ml Parr hydrogenation bottle charged with 1.0 g of a 10% palladium on carbon catalyst and 30 ml of isopropyl alcohol under a nitrogen atmosphere is added a mixture of 5.0 g of 1-benzyl-3-(α-phenyl-2-tolyl)-3-pyrrolidinol hydrochloride, Example 13, and 70 ml of isopropyl alcohol. The reaction mixture is hydrogenated at 50 psi with heating and shaking for 30 minutes. After hydrogenating the mixture is permitted to cool to ambient temperature and suction filtered. The filter cake is washed well with methanol and the methanol wash combined with the isopropyl alcohol filtrate. The combined wash and filtrate is evaporated leaving a solid which is recrystallized from isopropyl alcohol to leave colorless crystals, mp 211°–211.5° C. (dec), of 3-(α-phenyl-2-tolyl)-3-pyrrolidinol hydrochloride.

Analysis: Calculated for $C_{17}H_{19}NO \cdot HCl$: 70.44%C; 6.97%H; 4.83%N; 12.23%Cl. Found: 70.64%C; 7.09%H; 4.79%N; 12.27%Cl.

EXAMPLE 15

By following the manipulative procedure outlined above in Example 14, the hydrogenation of 1-benzyl-4-(α-phenyl-2-tolyl)-4-piperidinol.hydrochloride, Example 12, produces 4-(α-phenyl-2-tolyl)-4-piperidinol hydrochloride which is recrystallized from isopropyl alcohol with refrigeratio gives the salt as colorless crystals, mp 226°–227° C. (dec).

Analysis: Calculated for $C_{18}H_{21}NO \cdot HCl$: 71.15%C; 7.31%H; 4.61%N; 11.67%Cl. Found: 71.24%C; 7.43%H; 4.42%N; 11.53%Cl.

EXAMPLE 16

To a solution of 2.0 g of 1-(2-phenethyl)-4-(α-phenyl-2-tolyl)-4-piperidinol, Example 5, in 30 ml of tetrahydrofuran at −60° C. is added dropwise a solution of 2.8 ml of 2.4 M n-butyllithium in hexane. After total addition the reaction mixture is stirred for 15 minutes while maintaining this reduced temperature and then 1 ml of benzoyl chloride is added dropwise. The reaction mixture is permitted to stir at ambient temperature for 16 hours and then diluted with 40 ml of tetrahydrofuran and 10 ml of water. The biphasic mixture separates and the organic phase is washed successively with 10 ml of a 5% sodium hydroxide solution and 10 ml of water, treated with a slight excess of ethereal hydrogen chloride and then the solvent evaporated off. The oily residue is azeotropically dried with benzene and the solid residue is triturated with cold acetone, dissolved in chloroform and precipitated by gradual dilution with ether. The precipitate is dried to a colorless solid, mp 198°–203° C. of 4-benzoyloxy-1-(2-phenethyl)-4-(α-phenyl-2-tolyl)piperidine hydrochloride.

Analysis: Calculated for $C_{33}H_{33}NO_2 \cdot HCl$: 77.38%C; 6.71%H; 2.74%N. Found: 77.39%C; 6.90%H; 2.62%N.

EXAMPLE 17

A solution of 10.3 g of 1-benzyl-4-(α-phenyl-2-tolyl)-4-piperidinol hydrochloride, Example 12, in 70 ml of chloroform is washed twice with 50 ml portions of a 5% sodium hydroxide solution, dried and the chloroform evaporated off leaving the free base as an oil. The oil is dissolved in 10 ml of ether and treated carefully with 30 ml of acetylchloride. The resulting suspension is diluted with 30 ml of ether and stirred for 16 hours at ambient temperature. The precipitate is collected by filtration, washed well with ether and dried and then recrystallized from isopropyl alcohol to afford colorless crystals, mp 193°–194° C. of 4-acetoxy-1-benzyl-4-(α-phenyl-2-tolyl)piperidine hydrochloride.

Analysis: Calculated for $C_{27}H_{29}NO_2 \cdot HCl$: 74.37%C; 6.95%H; 3.21%N; 8.13%Cl. Found: 74.19%C; 6.99%H; 3.14%N; 8.28%Cl.

EXAMPLE 18

1.41 g of 1-methyl-4-(α-phenyl-2-tolyl)-4-piperidinol, Example 1, is treated with 4.0 ml of acetyl chloride with cooling and stirring. The resulting suspension is stirred at ambient temperature under nitrogen for one hour and then permitted to stand for 94 hours. The mixture is diluted with 10 ml of ether and filtered. The filter cake is washed with ether and then recrystallized from absolute ethanol to give colorless crystals, mp 205°–206° C. of 4-acetoxy-1-methyl-4-(α-phenyl-2-tolyl)piperidine hydrochloride.

Analysis: Calculated for $C_{21}H_{25}NO_2 \cdot HCl$: 70.07%C; 7.30%H; 3.89%N; 9.85%Cl Found: 70.25%C; 7.31%H; 3.87%N; 9.91%Cl.

EXAMPLE 19

2.0 g of 1-methyl-4-(α-phenyl-2-tolyl)-4-piperidinol, free base of Example 1, is treated with 8.15 ml of cyclopropane carboxylic acid chloride with stirring and cooling. The resulting suspension is stirred for 16 hours at ambient temperature and then diluted with 25 ml of ether and permitted to stand for 144 hours. The precipitate is collected by suction filtration and the filter cake washed with ether, dried in vacuo at 40° C. for 16 hours leaving colorless crystals which are recrystallized twice from isopropyl alcohol to give colorless crystals, mp 198°–200° C. of 4-cyclopropylcarbonyloxy-1-methyl-4-(α-phenyl-2-tolyl)piperidine hydrochloride.

Analysis: Calculated for $C_{23}H_{27}NO_2 \cdot HCl$: 71.57%C; 7.33%H; 3.63%N; 9.18%Cl. Found: 71.34%C; 7.50%H; 3.43%N; 9.02%Cl.

EXAMPLE 20

2.0 g of 1-methyl-4-(α-phenyl-2-tolyl)-4-piperidinol, Example 1, is treated with 10 ml of benzoyl chloride with stirring and cooling. The reaction solution is diluted with 20 ml of ether, stirred for two hours and the resulting precipitate collected by suction filtration. The filter cake is washed well with ether and dried in vacuo at 40° C. over sodium hydroxide pellets. The dried filter cake is recrystallized twice from a chloroform-ether mixture to give colorless crystals, mp 197°–198° C. of 4-benzoyloxy-1-methyl-4-(α-phenyl-2-tolyl)piperidine hydrochloride.

Analysis: Calculated for $C_{26}H_{27}NO_2 \cdot HCl$: 74.00%C; 6.70%H; 3.32%N; 8.40%Cl. Found: 74.04%C; 6.76%H; 3.36%N; 8.66%Cl.

EXAMPLE 21

2.0 g of 1-methyl-4-(α-phenyl-2-tolyl)-4-piperidinol, Example 1, is treated with 10 g of cyclobutanecarbonyl chloride with stirring and cooling. The reaction mixture is stirred for 48 hours at ambient temperature, diluted with 15 ml of ether and then stirred for 2 hours. The resulting precipitate is collected by suction filtration, the filter cake washed well with ether and dried in vacuo over sodium hydroxide pellets. The filter cake is recrystallized twice from an acetone-ether mixture to give colorless crystals, mp 194.5°–195° C. of 4-cyclobutylcarbonyloxy-1-methyl-4-(α-phenyl-2-tolyl)piperidine hydrochloride.

Analysis: Calculated for $C_{24}H_{28}NO_2 \cdot HCl$: 72.24%C; 7.34%H; 3.51%H; 8.88%Cl. Found: 72.02%C; 7.57%H; 3.41%H; 8.83%Cl.

EXAMPLE 22

1.41 g of 1-methyl-4-(α-phenyl-2-tolyl)-4-piperidinol, Example 1, is treated with 5.0 ml of propionyl chloride with stirring and cooling. The reaction mixture, at ambient temperature, is stirred for 30 minutes and then permitted to stand for 137 hours under nitrogen. The mixture is diluted with 5.0 ml of ether, stirred for 5 minutes and the resulting precipitate collected by suction filtration. The filter cake is washed thoroughly with ether and recrystallized twice from isopropyl alcohol to give colorless crystals, mp 191°–193° C. of 1-methyl-4-(α-phenyl-2-tolyl)-4-propionyloxypiperidine hydrochloride.

Analysis: Calculated for $C_{22}H_{27}NO_2 \cdot HCl$: 70.65%C; 7.56%H; 3.75%N; 9.48%Cl. Found: 70.55%C; 7.65%H; 3.74%N; 9.57%Cl.

EXAMPLE 23

A solution of 1.49 g of 1-methyl-4-(α-phenyl-2-tolyl)-4-piperidinol, 4.5 ml of valeryl chloride and 30 ml of chloroform is stirred for 16 hours at ambient temperature. The solution is basified with a 5% sodium hydroxide solution and the basified solution is also stirred overnight at ambient temperature. The biphasic mixture separates and the organic portion is washed with water, dried and the solvent evaporated off leaving an oil. The oil is dissolved in absolute ethanol and converted to an oxalate salt. The solvent is evaporated off and the residue dried in vacuo for 7 days at 40° C. The dried product is recrystallized from absolute ethanol to give colorless crystals, mp 194°–196° C., of 1-methyl-4-(α-phenyl-2-tolyl)-4-valeryloxypiperidine oxalate.

Analysis: Calculated for $C_{24}H_{31}NO_2 \cdot C_2H_2O_4$: 68.55%C; 7.30%H; 3.08%N. Found: 68.29%C; 7.16%H; 3.07%N.

EXAMPLE 24

1.5 g of 1-methyl-4-[α-(2-fluoro-4-methylphenyl)-2-tolyl]-4-piperidinol, Example 4, is treated carefully with 7 ml of benzoyl chloride with stirring and cooling. The reaction mixture is stirred for 16 hours at ambient temperature and then diluted with 15 ml of ether. The resulting precipitate is filtered, washed with ether, converted to the free base which is column chromatographed on an alumina column using ether as the eluant. The free base is converted to its hydrogen chloride salt which is recrystallized from a methanol-acetone-ether mixture to give a white powder, mp 218°–219° C. of 4-benzoyloxy-4-[α-(2-fluoro-4-methylphenyl)-2-tolyl]-1-methylpiperidine hydrochloride.

Analysis: Calculated for $C_{27}H_{28}FNO_2 \cdot HCl$: 71.43%C; 6.44%H; 3.09%N. Found: 71.08%C; 6.55%H; 2.88%N.

EXAMPLE 25

By following the manipulative procedure outlined above in Example 24, 1.97 g of 1-methyl-4-[α-(2-fluoro-4-methylphenyl)-2-tolyl]-4-piperidinol, Example 4, is treated with 6.3 ml of propionyl chloride to produce 4-[α-(2-fluoro-4-methylphenyl)-2-tolyl]-4-propionyloxy-1-methylpiperidine hydrochloride which is recrystallized from an acetone-ether mixture affording a product having an mp of 183°–186° C.

Analysis: Calculated for $C_{23}H_{28}FNO_2 \cdot HCl$: 68.05%C; 7.20%H; 3.45%N; 8.74%Cl. Found: 67.89%C; 7.27%H; 3.42%N; 8.87%Cl.

EXAMPLE 26

A suspension of 5.0 g of 3-(α-phenyl-2-tolyl)-3-pyrrolidinol hydrochloride, Example 14, in 40 ml of methanol is diluted with water until a solution forms. The solution is treated with an excess of a 5% sodium hydroxide solution and then the methanol removed on a rotary evaporator leaving a suspension. The suspension is diluted with 50 ml of water and extracted successively with a 100 ml and a 20 ml portion of chloroform. The combined chloroform extracts are washed once with 50 ml of a 5% sodium hydroxide solution and twice with 50 ml portions of water and dried and the chloroform removed. The residue is subjected to azeotropic distillation with benzene and then dried in vacuo at 40° C. for 2 hours before being suspended in 30 ml of warmed chloroform containing 2.2 g of triethylamine. To this suspension is added dropwise 2.60 g of benzoyl chloride. After total addition, the resulting solution is stirred for 2 hours and then permitted to stand for 48 hours. The solution is diluted with 30 ml of chloroform, washed successively with a 50 ml portion of water and similar amount of a 5% sodium hydroxide and dried and the solvent removed leaving a tacky foam. The foam is dissolved in 60 ml of ether (warming may be required), and the solution filtered through glass wool. A precipitate forms which is collected by suction filtration and dried in vacuo at ambient temperature leaving a colorless solid, mp 113°–116° C., of 1-benzoyl-3-(α-phenyl-2-tolyl)-3-pyrrolidinol.

Analysis: Calculated for $C_{24}H_{23}NO_4$: 80.63%C; 6.50%H; 3.92%N. Found: 80.51%C; 6.62%H; 3.80%N.

EXAMPLE 27

A solution of 8.0 g of 1-methyl-4-(α-phenyl-2-tolyl)-4-piperidinol, Example 1, in 100 ml of 97% formic acid is refluxed with stirring for 16 hours. The solution is poured into 300 ml of water, made strongly basic with a 50% sodium hydroxide solution and the basic mixture extracted thrice with 100 ml of portions of chloroform. The combined chloroform extracts are dried and the chloroform removed leaving an oil. The oil is dissolved in 20 ml of dimethylsulfoxide. The solution is diluted with 250 ml of water leaving a cream colored solid which is recrystallized from dimethylsulfoxide to give colorless crystals, mp 55°–57.5° C. of 1-methyl-4-(α-phenyl-2-tolyl)-1,2,3,6-tetrahydropyridine.

Analysis: Calculated for $C_{19}H_{21}N$: 86.63%C; 8.05%H. Found: 86.75%C; 8.29%H.

EXAMPLE 28

A suspension of 3.0 g of 4-(α-phenyl-2-tolyl)-4-piperidinol hydrochloride, Example 15, in 25 ml of glacial acetic acid and 5 ml of concentrated hydrochloric acid is refluxed with stirring for 60 minutes. The solution is permitted to cool and then diluted with 100 ml of water and basified with a 50% sodium hydroxide solution. The alkaline solution is extracted thrice with 30 ml portions of chloroform and the combined chloroform extracts are dried and the chloroform removed leaving an oil which crystallizes upon standing. The crystals are recrystallized from hexane leaving cream colored crystals, mp 73°–75° C., of 4-(α-phenyl-2-tolyl)-1,2,3,6-tetrahydropyridine.

Analysis: Calculated for $C_{18}H_{19}N$: 86.69%C; 7.70%H. Found: 86.72%C; 7.85%H.

EXAMPLE 29

By following the manipulative procedure outlined above in Example 28, 2.86 g of 1-(2-phenethyl)-4-(α-phenyl-2-tolyl)-4-piperidinol, Example 5, is dehydrated and treated to obtain colorless crystals, mp 98°–100° C., of 1-(2-phenethyl)-4-(α-phenyl-2-tolyl)-1,2,3,6-tetrahydropyridine.

Analysis: Calculated for $C_{26}H_{27}N$: 88.32%C; 7.71%H; 3.69%N. Found: 88.55%C; 7.79%H; 3.93%N.

EXAMPLE 30

A mixture of 5.0 g of 1-methyl-4-[α-(4-methoxyphenyl)-2-tolyl]-4-piperidinol, Example 2, 30 ml of glacial acetic acid and 6 ml of concentrated hydrochloric acid is refluxed with stirring for 2 hours and then permitted to stand for 48 hours at ambient temperature. The reaction solution is poured into ice-water and then basified with a 50% sodium hydroxide solution. The basic solution is extracted twice with 200 ml portions of chloroform and the combined chloroform extracts are dried, filtered and the chloroform removed under partial vacuum leaving an oil. The oil is dissolved in ether and the hydrogen bromide salt precipitated. The precipitate is collected by suction filtration and dried in vacuo at 40° C. The dried precipitate is recrystallized from isopropyl alcohol to give, colorless crystals, mp 149°–152° C. of 1-methyl-4-[α-(4-methoxyphenyl)-2-tolyl]-1,2,3,6-tetrahydropyridine hydrobromide.

Analysis: Calculated for $C_{20}H_{23}NO \cdot HBr$: 64.17%C; 6.46%H; 21.35%Br. Found: 64.09%C; 6.51%H; 20.98%Br.

EXAMPLES 31 & 32

By following the manipulative procedure outlined above in Example 30, 2.30 g of 4-[α-(4-fluorophenyl)-2-tolyl]-1-methyl-4-piperidinol, Example 3, and 3.5 g of 1-benzyl-4-(α-phenyl-2-tolyl)-4-piperidinol hydrochloride, Example 12, are dehydrated and treated to provide 4-[α-(4-fluorophenyl)-2-tolyl]-1-methyl-1,2,3,6-tetrahydropyridine hydrobromide and 1-benzyl-4-(α-phenyl-2-tolyl)-1,2,3,6-tetrahydropyridine hydrochloride, respectively, as listed in Table 2 sequentially as Examples 31 and 32.

TABLE 2

| | | | Analysis | | | | |
|---|---|---|---|---|---|---|---|
| | | | Calculated | | | Found | |
| Ex. | m.p. °C. | Empirical Formula | % C | % H | % N | % C | % H | % N |
| 31 | 192–196 | $C_{19}H_{20}FN \cdot HBr$ | 62.99 | 5.84 | 3.87 | 62.76 | 5.91 | 3.76 |
| 32 | 216–223 | $C_{25}H_{25}N \cdot HCl$ | 79.86 | 6.98 | 9.43 | 80.10 | 7.02 | 9.58 |

EXAMPLE 33

A suspension of 0.70 g of platinum oxide (Adam's catalyst) in 50 ml of 95% ethanol is hydrogenated on a Parr shaker at 50 psi for three hours at ambient temperature. To this hydrogenated suspension is added a solution of 2.4 g of 1-methyl-4-(α-phenyl-2-tolyl)-1,2,3,6-tetrahydropyridine, Example 27, in 50 ml of 95% ethanol and the resulting mixture is hydrogenated in similar fashion overnight. The mixture is filtered and the filtrate evaporated to a colorless oil which is taken up in ether. The ethereal solution is filtered, the filtrate treated with ethereal hydrogen chloride which causes a hydrogen chloride salt to precipitate. The salt is collected by suction filtration which is recrystallized twice from isopropyl alcohol to provide colorless crystals, mp 220.5°–222.5° C., of 1-methyl-4-(α-phenyl-2-tolyl)-piperidine hydrochloride.

Analysis: Calculated for $C_{19}H_{23}N \cdot HCl$: 75.59%C; 8.03%H; 11.74%Cl. Found: 75.40%C; 8.08%H; 11.57%Cl.

EXAMPLE 34

A suspension of 0.3 g of platinum oxide and 10 ml of absolute ethanol is hydrogenated on a Parr apparatus at ambient temperature at 50 psi for 15 minutes. To the hydrogenated suspension is added a solution of 3.1 g of 1-phenethyl-4-(α-phenyl-2-tolyl)-1,2,3,6-tetrahydropyridine, Example 29, in 100 ml of absolute ethanol. The reaction suspension is hydrogenated in similar fashion for 48 hours. The suspension is filtered and the filtrate treated with anhydrous hydrogen bromide. The filtrate is concentrated on a rotary evaporator leaving an oil which solidifies upon standing. The solid is recrystallized from 150 ml of hot absolute ethanol followed by gradual dilution with 350 ml of ether provides colorless crystals, mp 220°–225° C. of 1-phenethyl-4-(α-phenyl-2-tolyl)piperidine hydrobromide.

Analysis: Calculated for $C_{26}H_{29}N \cdot HBr$: 71.55%C; 6.93%H; 3.21%N. Found: 71.54%C; 7.11%H; 3.12%N.

EXAMPLE 35

A suspension of 0.5 g of platinum oxide and 25 ml of 95% ethanol is hydrogenated at 40 psi for 30 minutes at ambient temperature. To the hydrogenated suspension is added a solution of 2.5 g of 4-(α-phenyl-2-tolyl)-1,2,3,6-tetrahydropyridine, Example 28, in 25 ml of 95% ethanol and the reaction suspension is hydrogenated in similar fashion for 24 hours. The hydrogenated suspension is suction filtered and the filtrate evaporated to a colorless oil. Hydrogenation is repeated on this oil. The oil obtained after the second hydrogenation is converted to the hydrochloride salt. The salt is subjected to hydrogenation using 400 mg of platinum oxide at 50 psi. The salt is then recrystallized from 30 mml of isopropyl alcohol leaving colorless crystals, mp 207.5°–209.5° C., of 4-(α-phenyl-2-tolyl)piperidine hydrochloride.

Analysis: Calculated for $C_{18}H_{21}N \cdot HCl$: 75.10%C; 7.72%H; 4.87%N. Found: 75.13%C; 7.71%H; 4.80%N.

EXAMPLE 36

A mixture of 36.6 g of 4-[α-(4-methoxyphenyl)-2-tolyl]-1-methyl-1,2,3,6-tetrahydropyridine hydrobromide, Example 30, 153 ml of absolute methanol and 1.5 g of platinum oxide is hydrogenated at 50 psi at ambient temperature for 48 hours. The suspension is suction filtered while still hot through a sintered glass Buchner funnel and the filter cake is washed with several portions of hot chloroform. The filtrate and the washings are combined and then the solvent removed leaving a solid which is dried in vacuo at 40° C. for 16 hours. The solid is recrystallized from chloroform and the first five crops are dried in an Abderhalden pistol over xylene for 32 hours leaving colorless crystals, mp 182°–185° C., of 4-[α-(4-methoxyphenyl)-2-tolyl]-1-methylpiperidine hydrobromide.

Analysis: Calculated for $C_{20}H_{25}NO \cdot HBr$: 63.83%C; 6.96%H; 3.72%N. Found: 63.97%C; 7.06%H; 3.87%N.

EXAMPLE 37

A solution of 24.9 g of 1-methyl-4-[α-phenyl-2-tolyl)-piperidine hydrochloride, Example 33, in 100 ml of methylene chloride is washed twice with 50 ml portions of a 5% sodium hydroxide solution. The methylene chloride solution is dried and filered and then a solution of 14.1 g of phenyl chloroformate in 100 ml of methylene chloride is added dropwise with stirring over a 40 minute span. The solution is permitted to stir for 16 hours and then the solvent evaporated off leaving a solid residue. The residue is suspended in ether and collected by suction filtration. The filter cake is washed with ether and dried in vacuo at 40° C. over sodium hydroxide pellets. The dried filter cake is recrystallized from isopropyl alcohol leaving colorless crystals, mp 120°–122° C. of 4-(α-phenyl-2-tolyl)-1-phenoxycarbonylpiperidine.

Analysis: Calculated for $C_{25}H_{25}NO_2$: 80.82%C; 6.80%H; 3.77%N. Found: 80.99%C; 6.80%H; 3.69%N.

EXAMPLE 38

A mixture of 6.89 g of 4-[α-(4-methoxyphenyl)-2-tolyl]-1-methylpiperidine, free base of Example 36, 85 ml of methylene chloride and 4.0 g of phenyl chloroformate is stirred for 16 hours. Then the solvent is removed on a rotary evaporator and the residue azeotroped with benezene. The solid residue is dried in vacuo at 40° C. and recrystallized from absolute ethanol leaving colorless crystals, mp 116°–118° C. of 4-[α-(4-methoxyphenyl)-2-tolyl]-1-phenoxycarbonylpiperidine.

Analysis: Calculated for $C_{26}H_{27}NO_3$: 77.77%C; 6.79%H; 3.49%N. Found: 77.85%C; 6.83%H; 3.46%N.

EXAMPLE 39

A stirring suspension of 4.0 g of 4-[α-(4-methoxyphenyl)-2-tolyl]-1-phenoxycarbonylpiperidine, Example 38, 110 ml of ethylene glycol and 14 ml of a solution prepared from 20 g of potassium hydroxide pellets in 22 ml of water is heated to reflux and then allowed to cool to ambient temperature followed by ice bath cooling to effect a precipitate. The precipitate is collected by filtration and dissolved in 100 ml of chloroform. The solution is washed with water, dried and filtered and the filtrate treated with an excess of hydrogen chloride gas. The solvent is removed on a rotary evaporator and the residue dried in vacuo at 40° C. leaving a crude solid which is recrystallized from ethanol leaving colorless crystals, mp 246°–248° C. of 4-[α-(4-methoxyphenyl)-2-tolyl]-piperidine hydrochloride.

Analysis: Calculated for $C_{19}H_{23}NO.HCl$: 71.79%C; 7.61%H; 4.41%N. Found: 72.00%C; 7.75%H; 4.51%N.

EXAMPLE 40

A solution of 5.37 g of 4-(α-phenyl-2-tolyl)piperidine hydrochloride, Example 35, in 50 ml of chloroform is washed with an excess of a 5% sodium hydroxide solution and dried and the solvent removed leaving a viscous oil. The oil is dissolved in 10 ml of benzene and added dropwise with stirring and ice-water bath cooling to a solution of 2.28 g of benzoyl peroxide in 75 ml of benzene. After total addition the reaction solution is stirred with ice-water bath cooling for 10 minutes and at the ambient temperature for 2.5 hours. The solution is concentrated on a rotary evaporator at 40° C. leaving an oil which is dissolved in 95% ethanol. The ethanolic solution is maintained at 5° C. for 48 hours with occassional stirring. After this time a crystalline precipitate is present which is collected by suction filtration, washed with 95% ethanol and dried in vacuo at 40° C. The dried product is recrystallized from 95% ethanol leaving cream colored crystals, mp 102°–103° C. of 1-benzoyloxy-4-(α-phenyl-2-tolyl)piperidine.

Analysis: Calculated for $C_{25}H_{25}NO_2$: 80.82%C; 6.80%H; 3.77%N. Found: 80.74%C; 6.86%H; 3.75%N.

EXAMPLE 41

A suspension of 2.63 g of 1-benzoyloxy-4-(α-phenyl-2-tolyl)piperidine, 25 ml of absolute ethanol and 20 ml of a 10% sodium hydroxide solution heated on a water bath at 100° C. for 40 minutes. After this time the suspension is permitted to cool to ambient temperature, stirred at ambient temperature for 1.5 hours and then concentrated on a rotary evaporator to ⅓ of its original volume. The reaction solution is diluted with 50 ml of water and its pH adjusted to 6.0 with 5% hydrochloric acid leaving a suspension which is extracted twice with 50 ml portions of chloroform. The combined extracts are dried and the solvent removed leaving a solid residue which is recrystallized from 95% ethanol leaving colorless crystals, mp 142°–147° C. of 1-hydroxy-4-(α-phenyl-2-tolyl)piperidine.

Analysis: Calculated for $C_{18}H_{21}NO$: 80.85%C; 7.93%H; 5.24%N. Found: 80.79%C; 8.04%H; 5.07%N.

EXAMPLE 42

A stirring mixture of 6 g of 1-methyl-4-[α-(4-methoxyphenyl)-2-tolyl]piperidine hydrobromide, Example 36, and 9.6 ml of a 48% hydrobromide solution is immersed in an oil bath (140° C.) for 30 minutes. The hot solution is poured into cold water and 174 ml of concentrated ammonium hydroxide is added effecting a precipitate. The precipitate is collected by filtration and the filter cake dried overnight in vacuo at ambient temperature. The dried precipitate is recrystallized from absolute ethanol leaving a pinkish crystalline solid, mp 229°–232° C. of 4-[α-(4-hydroxyphenyl-2-tolyl]-1-methylpiperidine.

Analysis: Calculated for $C_{19}H_{23}NO$: 81.11%C; 8.31%H; 4.95%N; 5.41%O. Found: 81.10%C; 8.24%H; 4.98%N; 5.69%O.

EXAMPLE 43

To a stirring refluxing suspension of 5.76 g of 4-(α-phenyl-2-tolyl)piperidine hydrochloride, Example 35, 18.0 g of potassium carbonate and 70 ml of n-butyl alcohol is added dropwise 8.70 g of 2-(3-chloropropyl)-2-(4-fluorophenyl)-1,3-dioxolane. After total addition the reaction mixture is refluxed with stirring for 16 hours, filtered and then the filtrate is concentrated to dryness leaving an oil which is dissolved in 75 ml of ether. The ether solution is filtered and the filtrate treated with ethereal hydrogen chloride. An oil separates as the lower phase which is washed twice with portions of ether and then dissolved in chloroform. The chloroform solution is evaporated to dryness leaving a tacky foam which is redissolved in 15 ml of chloroform and this solution diluted to the cloud point with ether. The mixture is stirred until a thick suspension is formed which is diluted with 20 ml of ether. A precipitate appears which is collected by suction filtration. The filter cake is washed well with ether followed by recrystallization from isopropyl alcohol leaving colorless crystals, mp 185°–187.5° C. of 1-[3-(4-fluorobenzoyl)propyl]-4-(α-phenyl-2-tolyl)piperidine ethylene ketal hydrochloride.

Analysis: Calculated for $C_{30}H_{34}FNO_2.HCl$: 72.63%C; 7.13%H; 2.82%N. Found: 72.62%C; 7.20%H; 2.79%N.

EXAMPLE 44

A stirred solution of 3.0 g of 1-[3-(4-fluorobenzoyl)propyl]-4-(α-phenyl-2-tolyl)piperidine ethylene ketal hydrochloride, Example 43, 100 ml of methanol and 50 ml of concentrated hydrochloric acid is refluxed for 2 hours. The hot solution is poured onto ice, and the reaction mixture basified with a 50% sodium hydroxide solution, and the basic mixture extracted thrice with 100 ml portions of chloroform. The combined extracts are dried and the solvent evaporated off leaving an oil. The oil is taken up in 5 ml of hexane and stirring of the hexane solution effects a thick suspension of crystalline solid which is collected by suction filtration. The solid is recrystallized from acetonitrile to give colorless crystals, mp 100°–101.5° C. of 1-[3-(4-fluorobenzoyl)propyl]-4-(α-phenyl-2-tolyl)piperidine.

Analysis: Calculated for $C_{28}H_{30}FNO$: 80.92%C; 7.29%H; 4.57%F; 3.37%N. Found: 81.07%C; 7.37%H; 4.72%F; 3.32%N.

EXAMPLE 45

A solution of 1.4 g of 4-[α-(2-fluoro-4-methylphenyl)-2-tolyl]-1-phenethyl-4-piperidinol, Example 11, in 30 ml of tetrahydrofuran is cooled to −60° C. To this cooled solution is added 1.5 ml of n-butyllithium and the resulting solution stirred for 15 minutes. To this solution is added dropwise 0.3 ml of propionyl chloride at this low temperature and after total addition the solution is permitted to reach ambient temperature. The solution is stirred at ambient temperature for 24 hours. The solution is diluted with water and extracted with chloroform. The chloroform extract is dried and filtered and the chloroform evaporated off leaving a white powder. The powder is recrystallized from a methanol-acetone-ether mixture to give the product, mp 195°–197° C. of 4-[α-(2-fluoro-4-methylphenyl)-2-tolyl]-4-propionyloxy-1-phenethylpiperidine hydrochloride.

Analysis: Calculated for $C_{30}H_{34}FNO_2 \cdot HCl$: 72.63%C; 7.11%H; 2.82%N. Found: 73.08%C; 7.35%H; 2.65%N.

EXAMPLE 46

A mixture of 3 g of 4-[α-(4-methoxyphenyl)-2-tolyl]-piperidine hydrochloride, Example 39, and 48 ml of 48% HBr is refluxed on an oil bath (157° C.) with stirring for 32 minutes, cooled and then poured onto 48 ml of cooled water. The resulting suspension is quenched with 48 ml of concentrated ammonium hydroxide, stirred thoroughly and the solid is collected by suction filtration. The filter cake is dried in vacuo at 40° C. over sodium hydroxide pellets and then dissolved in 500 ml of hot absolute ethanol. 32 ml of triethylamine is added to the hot ethanolic solution. The hot solution is diluted with chloroform and then washed twice with water. The organic phase is collected, dried and filtered and then the solvent evaporated off leaving a solid product which is recrystallized from absolute ethanol in the presence of activated charcoal to give yellowish crystals, mp 217°–221° C. of 4[α-(4-hydroxyphenyl)-2-tolyl]piperidine.

Analysis: Calculated for $C_{18}H_{21}NO$: 80.86%C; 7.92%H; 5.24%N. Found: 80.75%C; 7.89%H; 5.10%N.

EXAMPLE 47

A mixture of 4 g of 4-[α-(4-fluorophenyl)-2-tolyl]-1-methyl-1,2,3,6-tetrahydropyridine hydrobromide, Example 31, 0.3 g of platinum oxide and 150 ml of methanol is hydrogenated at 50 psi at ambient temperature for 48 hours. After which time the suspension is suction filtered and the filtrate evaporated under reduced pressure. The solid residue is collected and dried in vacuo at 40° C. and then recrystallized from isopropanol to give colorless crystals, mp 183°–186° C., of 4-[α-(4-fluorophenyl)-2-tolyl]-1-methylpiperidine hydrobromide.

Analysis: Calculated for $C_{19}H_{22}FN \cdot HBr$: 62.66%C; 6.36%H; 3.85%N; 5.22%F. Found: 62.81%C; 6.39%H; 3.94%N; 5.06%F.

EXAMPLE 48

A mixture of 28.6 g of 4-[α-(4-fluorophenyl)-2-tolyl]-1-methylpiperidine, free base of Example 47, 85 ml of methylene chloride and 17.2 g of phenyl chloroformate is stirred for 16 hours at ambient temperature followed by distillation of solvent on a rotary evaporator and azeotropic distillation of the residue with benzene. The resulting oil solidifies upon trituration with ether. The solid is recrystallized from absolute ethanol to give colorless crystals, mp 107°–110° C., of 4-[α-(4-fluorophenyl)-2-tolyl]-1-phenoxycarbonylpiperidine.

Analysis: Calculated for $C_{25}H_{24}FNO$: 77.10%C; 6.21%H; 3.60%N. Found: 77.00%C; 6.18%H; 3.59%N.

EXAMPLE 49

A mixture of 500 ml of ethylene glycol, a solution of 60 g of potassium hydroxide in 66 ml of water and 16.6 g of 4-[α-(4-fluorophenyl)-2-tolyl]-1-phenoxycarbonylpiperidine, Example 48, is gradually heated to 200° C. with constant stirring and allowed to reflux. The mixture is then allowed to cool, flushed with nitrogen and allowed to stand for 48 hours. The mixture is suction filtered, and the filter cake dissolved in chloroform. To the chloroform solution water is added and extracted with ether. The combined extracts are dried, filtered and then treated with gaseous hydrobromic acid. The solvent is evaporated under reduced pressure to give a solid which is recrystallized twice from isopropanol to give colorless crystals, mp 227°–231° C., of 4-[α-(4-fluorophenyl)-2-tolyl]piperidine hydrobromide.

Analysis: Calculated for $C_{18}H_{20}FN \cdot HBr$: 61.72%C; 6.04%H; 4.00%N; 5.42%F. Found: 61.95%C; 5.88%H; 3.99%N; 5.43%F.

EXAMPLE 50 a. 5 g of the free base of 4-(α-phenyl-2-tolyl)-4-piperidinol hydrochloride of Example 15 which is obtained by treating an alcoholic solution of the salt with aqueous NaOH and extracting with $CH_2Cl_2$, followed by drying ($Na_2SO_4$) and evaporating at reduced pressure, is combined with 70 ml of ethyl formate, 79 ml of ethanol, and then refluxed for 3 hours. The solvent is evaporated at reduced pressure and the material is collected and recrystallized to give colorless crystals, mp 171°–174° C. of 1-formyl-4-(α-phenyl-2-tolyl)-4-piperidinol.

Analysis: Calculated for $C_{19}H_{21}NO_2$: 77.26%C; 7.17%H; 4.74%N. Found: 77.31%C; 7.33%H; 4.55%N.

b. A mixture of 1-formyl-4-(α-phenyl-2-tolyl)-4-piperidinol (13.61 g), potassium (2.92 g) and 341 ml of sieve dried toluene is heated to reflux under $N_2$ and the temperature is then lowered to 86° C. Methyl iodide (66.7 g) is added and the mixture is stirred 16 hours at 83° C. The mixture is quenched with a large excess of water, filtered and the phases are separated. The organic phase is washed with water and the combined aqueous phases are back-washed with toluene. The combined organic phase is dried ($Na_2SO_4$), filtered, and evaporated under reduced pressure. Dilution with ether and further evaporation under reduced pressure gives an oil which solidifies and is then briefly dried in vacuo at 36° C. The solid is crystallized from ethanol-ether to give crystals which are washed with 90% ether-hexane and triturated in hexane to give, after filtration and drying at 36° C. for 16 hours, 1-formyl-4-methoxy-4-(α-phenyl-2-tolyl)piperidine, mp 88°–95° C. The mother liquor is diluted with hexane and on standing affords additional crystalline material which is identified as starting material. After removal of the starting material, the mother liquor is evaporated and the residue dissolved in ethanol. Dilution with ether, and 90% ether-hexane and trituration with hexane gives on drying in vacuo at 36° C., 1-formyl-4-methoxy-4-(α-phenyl-2-tolyl)piperidine.

Analysis: Calculated for $C_{20}H_{23}NO_2$: 77.64%C; 7.49%H. 4.53%N. Found: 77.65%C; 7.67%H; 4.36%N.

EXAMPLE 51

A mixture of 3.3 g of potassium hydroxide and 25 ml of methanol is heated and to the resulting solution is added 1.16 g of 1-formyl-4-methoxy-4-(α-phenyl-2-toyl)piperidine of Example 50 b and the cooled solution is then diluted with water and extracted with ether. The ether is dried with $K_2CO_3$ and gravity filtered. The resultant oil is evaporated under reduced pressure to give an oily, semi-solid. The oil is recrystallized by dissolving in cyclohexane, gravity filtering, partially evaporating at reduced pressure and seeding. The solid is triturated with a small amount of cyclohaxane and collected by suction filtration. After brief drying in vacuo at 40° C. a yield of crystals of 4-methoxy-4-(αphenyl-2-tolyl)piperidine is obtained, mp 87°–89° C.

Analysis: Calculated for $C_{19}H_{23}NO$: 81.10%C; 8.24%H; 4.98%N. Found: 80.80%C; 7.98%H; 4.76%N.

EXAMPLE 52

To a stirred mixture of 4.0 g of 1-formyl-4-methoxy-4-(α-phenyl-2-tolyl)piperidine, of Example 50 b, in 300 ml of anhydrous ether, 0.68 g of 95% lithium aluminum hydride and 100 ml of anhydrous ether is added dropwise the solution of 1-formyl-4-methoxy-4-(α-phenyl-2-tolyl)piperidine, followed by stirring 16 hours at room temperature. The resultant mixture is quenched under $N_2$ with distilled water. The mixture is gravity filtered, the phases are separated and the aqueous phase is further extracted with ether. The combined organic phase is dried ($K_2CO_3$), filtered and evaporated to give an oil. The oil is dissolved in ether, cooled and acidified wth ethereal HCl. After 15 minutes of stirring, a crystalline precipitate is collected by suction filtration and dried in vacuo at 40° C. Recrystallization of the filter cake from absolute ethenol affords colorless crystals, mp 238°–239° C. of 1-methyl-4-methoxy-4-(α-phenyl-2-tolyl)piperidine.

Analysis: Calculated for $C_{20}H_{25}NO.HCl$: 72.38%C; 7.90%H; 4.22%N; 10.68%Cl. Found: 72.04%C; 8.03%H; 3.90%N; 10.67%Cl.

EXAMPLE 53 a. A mixture of 5.00 g of 3-(α-phenyl-2-tolyl)-3-pyrrolidine of Example 14 in 120 ml of ethyl formate is refluxed for 5⅔ hours. The solvent is removed under reduced pressure to a total volume of approximately 20 ml and the solution is diluted with 100 ml of ether and cooled 16 hours. The crystals are collected by filtration, washed with ether, and dried to give 3-hydroxy-1-methyl-3-(α-phenyl-2-tolyl)pyrrolidine, mp 127°–128° C.

Analysis: Calculated for $C_{18}H_{19}NO_2$: 76.84%C; 6.81%H; 4.98%N. Found: 76.62%C; 6.60%H; 4.89%N.

b. A solution of 5.90 g of 1-formyl-3-hydroxy-3-(α-phenyl-2-tolyl)pyrrolidine in 60 ml of dry THF is added dropwise to a suspension of 3 g of LiAlH in 30 ml of dry THF and the mixture is refluxed for 4 hours. After cooling the mixture is separated and the residue extracted with ether. The combined organic solution is dried ($Na_2SO_4$) and concentrated to an oil. This oil is dissolved in 100 ml of hexane and after cooling 16 hours the product is isolated by filtration to provide 3-hydroxy-1-methyl-3-(α-phenyl-2-tolyl)pyrrolidine, mp 108°–109° C. Dilution of the mother liquor with 50 ml of hexane gives a second crop of 3-hydroxy-1-methyl-3-(α-phenyl-2-tolyl)pyrrolidine, mp 107°–108° C.

Analysis: Calculated for $C_{18}H_{21}NO$: 80.86%C; 7.92%H; 5.24%N. Found: 80.69%C; 7.92%H; 4.96%N.

EXAMPLE 54

A solution of 2.60 g of 3-hydroxy-1-methyl-3-(α-phenyl-2-tolyl)pyrrolidine of Example 53, in 30 ml of acetic acid and 2 ml of $BF_3$.ether is stirred at 50°–60° C. for 2½ hours and 16 hours at room temperature. The mixture is diluted with 30 ml of $H_2O$, is made alkaline with NaOH, and extracted with $CH_2Cl_2$. The $CH_2Cl_2$ solution is dried ($Na_2SO_4$) and concentrated to an oil. A portion of the oil is dissolved in 10 ml of acetic acid and stirred with 0.7 ml of $H_2SO_4$ at 55° C. for 2 hours. A solution of the resultant oil in 15 ml of acetone is heated with 1.1 g of fumaric acid for dissolving and after cooling a product is isolated and recrystallized from acetone (60 ml) to provide 1-methyl-3-(α-phenyl-2-tolyl)-3-pyrrolie fumarate, mp 131°–132.5° C.

Analysis: Calculated for $C_{18}H_{19}N.C_4H_4O_4$: 72.31%C; 6.34%H; 3.83%N. Found: 72.28%C; 6.52%H; 3.61%N.

EXAMPLE 55

A mixture of 3.77 g of 1-benzyl-3-(α-phenyl-2-tolyl)-pyrrolidinol hydrochloride of Example 13, 15 ml of acetic acid and 1.5 ml of concentrated HCl is heated under reflux for 85 minutes. After this, the solvents are removed under reduced pressure and the remaining oil is distributed between $CH_2Cl_2$ and 5% NaOH. The organic layer is washed with water, dried ($Na_2SO_4$), and evaporated to give an oil. This oil is crystallized from acetone-methanol (10 ml–20 ml) to provide a product which is recrystallized from acetone-methanol (1 ml–3 ml) to yield 1-benzyl-3-(α-phenyl-2-tolyl)-2-pyrroline, mp 75°–76° C.

Analysis: Calculated for $C_{24}H_{23}N$: 88.57%C; 7.12%H; 4.30%N. Found: 88.30%C; 7.12%H; 4.10%N.

EXAMPLE 56 a. 4.29 g of 3-(α-phenyl-2-tolyl)-3-pyrrolidinol hydrochloride of Example 14 is stirred for 1 hour with a mixture of 50 ml of water, 350 ml $CHCl_3$, and 0.66 g of NaOH. The organic phase is separated, dried ($Na_2SO_4$), filtered, and 1.81 g of TEA is added. After cooling (0° C.) a solution of 1.70 g cyclopropanecarboxylic acid chloride in 10 ml $CHCl_3$ is added dropwise with stirring at 0° C. After two hours at 0° C., three hours at room temperature, and 16 hours at 5° C., the solution is washed, dried ($Na_2SO_4$), filtered, and evaporated to an oil. This oil is dissolved in 50 ml ether and after one hour at room temperature crystals are collected by suction filtration, washing with ether to yield colorless crystals of 1-cycloproylmethyl-3-hydroxy-3-(α-phenyl-2-tolyl)pyrrolidine, mp 118°–120° C.

Analysis: Calculated for $C_{21}H_{23}NO_2$: 78.47%C; 7.21%H; 4.36%N. Found: 78.60%C; 7.09%H; 4.15%N.

b. To a solution of 45 ml of 1 M-borane in THF is added under dry nitrogen at 0° C., 6.36 g 1-cyclopropylcarbonyl-3-hydroxy-3-(α-phenyl-2-tolyl)pyrrolidine in 20 ml of dry THF. The solution is then brought to reflux and maintained there for 1 hour. The solution is permitted to cool to room temperature and 3.3 ml of 6 N-HCl is added slowly. The THF is removed by distillation at atmospheric pressure and the residue is crystallized with 50 ml of anhydrous ether and recrystallized from methanol/ether (30 ml/80 ml) to give colorless crystals. The mother liquid is made acid with a slight excess of HCl/ether and a second crop is obtained by suction filtration. The mother liquid is concentrated in vacuo to an oil and a third crop is obtained by crystallization with ether. Recrystallization from methanol/ether (20 ml/50 ml) yields 1-cyclopropylmethyl-3-hydroxy-3-(α-phenyl-2-tolyl)pyrrolidine hydrochloride, mp 168°–169° C.

Analysis: Calculated for $C_{21}H_{26}ClNO$: 73.35%C; 7.62%H; 4.07%N; 10.31%Cl. Found: 73.38%C; 7.70%H; 4.14%N; 10.70%Cl.

EXAMPLE 57

Acetyl chloride (1.57 g) is added at 0° C. to a solution of (3.16 g) of pyridine in 20 ml of $CH_2Cl_2$ and this mixture is stirred at 0° C. for 15 minutes. To this mixture is added at 0° C. a solution of 0.01 mole of 1-benzyl-3-(α-phenyl-2-tolyl)pyrrolidinol (the free base of Example 13) in about 40 ml of CH$_2$Cl$_2$ and the resulting mixture is boiled for 1 hour and 20 minutes. After standing 16 hours (5° C.) the solution is washed with water, dried (Na$_2$SO$_4$), and evaporated to an oil. This oil is dissolved in 40 ml of ethanol and 0.99 g oxalic acid are added with stirring. After one hour 20 ml of ether are added, and the resultant product is collected by suction filtration, recrystallized from ethanol/ether (40 ml/20 ml), and dried over P$_2$O$_5$ for 10 hours at 40° C. to yield 3-acetoxy-1-benzyl-3-(α-phenyl-2-tolyl)pyrrolidine oxalate, mp 163°–164° C.

Analysis: Calculated for C$_{28}$H$_{29}$NO$_6$: 70.72%C; 6.15%H; 2.95%N. Found: 70.50%C; 6.23%H; 2.96%N.

EXAMPLE 58

25.9 g of 3-acetoxy-1-benzyl-3-(α-phenyl-2-tolyl)pyrrolidine oxalate of Example 57 is suspended at 0° C. in 500 ml CH$_2$Cl$_2$ and stirred with a slight excess of 5% NaOH for ½ hour. The organic layer is washed with water, dried (Na$_2$SO$_4$), and concentrated to an oil. This oil is dissolved in 200 ml of i-propanol and the solution is made acidic with a very slight excess of HCl/i-propanol and hydrogenated with 5 g of Pd on carbon (10%) at 70° C. and 60 psig for 8 hours. After filtration the solution is diluted with 700 ml of ether and after cooling the product is collected by filtration. Recrystallization from methanol-ether (40 ml-160 ml) provides 3-(α-phenyl-2-tolyl)pyrrolidine hydrochloride, mp 148°–149° C.

Analysis: Calculated for C$_{17}$H$_{19}$N.HCl: 74.57%C; 7.36%H; 5.12%N. Found: 74.40%C; 7.37%H; 5.06%N.

EXAMPLE 59

A solution of 3.42 g of 3-(α-phenyl-2-tolyl)pyrrolidine hydrochloride of Example 58 in 50 ml of CH$_2$Cl$_2$ is stirred with an excess of 5% NaOH. The organic phase is separated, washed with water, dried (Na$_2$SO$_4$), and evaporated to an oil. This oil is dissolved in 50 ml of ethyl formate and refluxed for 18 hours. The solvent is removed under reduced pressure to give an oil, which is dissolved in 25 ml of ether, and after cooling 16 hours the product is collected by filtration to provide 1-formyl-3-(α-phenyl-2-tolyl)pyrrolidine, mp 70°–71° C.

Analysis: Calculated for C$_{18}$H$_{19}$NO: 81.47%C; 7.22%H; 5.28%N. Found: 81.53%C; 7.20%H; 5.12%N.

EXAMPLE 60

A solution of 3.42 g of 3-(α-phenyl-2-tolyl)pyrrolidine hydrochloride, of Example 58, in 50 ml of CH$_2$Cl$_2$ is stirred with an excess of 5% NaOH. The organic layer is separated, washed with water, dried (Na$_2$SO$_4$), and cooled to 0° C. To this solution is added 1.52 g of (C$_2$H$_5$)$_3$N and dropwise a solution of 1.46 g of cyclopropanecarbonyl chloride in 10 ml of CH$_2$Cl$_2$. The solution is kept 16 hours at 5° C., washed with water, 5% NaOH, 5% HCl, and water, dried (Na$_2$SO$_4$), and evaporated to an oil. A solution of this oil in 60 ml of dry THF is added dropwise to a mixture of 1.5 g LiAlH in 20 ml of dry THF and the mixture is refluxed for 4 hours. After cooling the mixture is hydrolyzed with 50 ml of water and the organic phase is separated. The aqueous phase is extracted with ether and the combined organic layers are washed with water, dried (Na$_2$SO$_4$), and evaporated to an oil. This oil is dissolved in 20 ml of methanol and 1.62 g of fumaric acid is added. The clear solution is diluted with 100 ml of ether and the product is collected by filtration. This product is recrystallized from methanol-ether (25 ml–75 ml) to provide 1-cyclopropylmethyl-3-(α-phenyl-2-tolyl)pyrrolidine fumarate, mp 124°–126° C.

Analysis: Calculated for C$_{21}$H$_{25}$N.C$_4$H$_4$O$_4$: 73.68%C; 7.17%H; 3.44%N. Found: 73.66%C; 7.26%H; 3.27%N.

EXAMPLE 61

A solution of 5.08 g of 3-(α-phenyl-2-tolyl)pyrrolidine hydrochloride, of Example 58, in 80 ml of CH$_2$Cl$_2$ is stirred with an excess of 5% NaOH. The organic laye is separated, dried (Na$_2$SO$_4$), filtered (charcoal, Celite), and concentrated in vacuo to an oil. A solution of this oil in 70 ml of DMF is stirred with 3.15 g of KI, 5.23 g of K$_2$CO$_3$, and 4.65 g of 4-chloro-p-fluoro-butyrophenone ethylene ketal at 90° C. for 21 hours. The solvent is removed under reduced pressure and the remaining oil is dissolved in 100 ml of CH$_2$Cl$_2$. The solution is washed with water, dried (Na$_2$SO$_4$), and concentrated to an oil. This oil is stirred with 80 ml of methanol, 20 ml of H$_2$O, and 10 ml of concentrated HCl. for 1.5 hours. The solvents are removed, the oil taken up in 100 ml of CH$_2$Cl$_2$, and the solution is washed with 5% NaOH and with H$_2$O, dried (Na$_2$SO$_4$), and concentrated to an oil. This oil is stirred with 2.2 g of maleic acid in 10 ml of methanol and 50 ml of ether at room temperature for 1 hour. The product is isolated and recrystallized from methanol/ether (30/100 ml) to provide 4'-fluoro-4-[3-(α-phenyl-2-tolyl)pyrrolidine-1-yl]butyrophenone, mp 126°–128° C.

Analysis: Calculated for C$_{27}$H$_{28}$FNO.C$_4$H$_4$O$_4$: 71.93%C; 6.23%H; 3.67%F; 2.71%N. Found: 71.78%C; 6.22%H; 3.85%F; 2.64%N.

EXAMPLE 62

A solution of 5.90 g of 1-formyl-3-(α-phenyl-2-tolyl)-pyrrolidine of Example 59 in 40 ml of dry THF is added dropwise to a suspension of 2 g LiAlH in 20 ml of dry THF and the mixture is refluxed for 4 hours. After cooling and hydrolyzing with 20 ml of H$_2$O the organic phase is separated and the residue is extracted with ether. The combined organic phase is washed with water, dried (Na$_2$SO$_4$), and concentrated to an oil. This oil is dissolved in 10 ml of acetone and made acidic with a slight excess of HCl/ether. After addition of 200 ml of ether the product is collected and recrystallized from acetone/ether (35/70 ml) to provide 1-methyl-3-(α-phenyl-2-tolyl)pyrrolidine, mp 149.5°–151° C.

Analysis: Calculated for C$_{18}$H$_{21}$N.HCl: 75.11%C; 7.70%H; 4.87%N. Found: 75.25%C; 7.65%H; 4.83%N.

EXAMPLE 63

4.40 g of 4-(α-phenyl-2-tolyl)piperidine hydrochloride of Example 35 and 14 g K$_2$CO$_3$ in 50 ml of n-butanol are heated to reflux with stirring. To this is added 5.66 g 3-phenoxypropylbromide in 10 ml of n-butanol dropwise. The mixture is then refluxed for 24 hours. After cooling the suspension is suction filtered, washing the flask and filter cake with n-butanol. The combined filtrates are evaporated to an oil which is dissolved in 20 ml of isopropanol and made acid with HCl/ether. The hydrochloride is collected by suction filtration and washed with ether. The resultant product is recrystallized from isopropanol/ether to yield 1-(3-phenoxypropyl)-4-(α-phenyl-2-tolyl)piperidine, mp 139°–140° C.

Analysis: Calculated for C₂₇H₃₁NO.HCl.H₂O: 73.70%C; 7.73%H; 3.18%N; 8.06%Cl. Found: 73.95%; 7.35%H; 3.11%N; 8.11%Cl.

We claim:

1. A compound of the formula

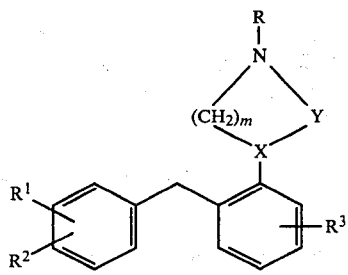

wherein X is COR⁵; Y is —(CH₂)ₙ—; R is hydrogen, loweralkyl, phenylloweralkyl of the formula

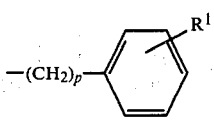

or cycloalkylloweralkyl in which the cycloalkyl portion contains from 3 to 6 carbon atoms; R¹, R² and R³ are the same or different and each can be hydrogen, halogen, alkoxy of from 1 to 2 carbon atoms, loweralkyl, hydroxy or trifluoromethyl; R⁵ is hydrogen, loweralkyl, carboxylic acid loweralkyl, benzoyl or carboxylic acid lowercycloacyl; m is the integer 1 or 2; n is the integer 1, 2 or 3; the sum of m and n is 3 or 4; p is the integer 1, 2, 3 or 4; or a pharmaceutically acceptable acid addition salt thereof.

2. A compound as defined in claim 1 wherein R³ is hydrogen.

3. A compound defined in claim 1 wherein R¹ and R² are the same or different and each can be hydrogen, fluorine, methyl or methoxy.

4. A compound defined in claim 2 wherein R is hydrogen or loweralkyl.

5. The compound as defined in claim 1 of the formula

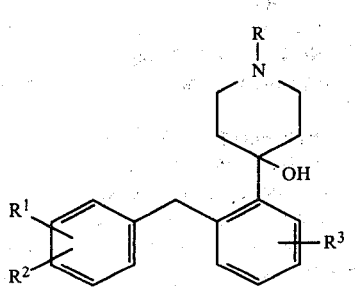

wherein
R is —H, lower alkyl, —CH₂φ, —CH₂CH₂φ, or —CH₂CH₂CH₂φ;
R¹ to R³ is H, hal, 1-2C alkoxy, —CF₃, or lower alkyl;
or a pharmaceutically acceptable acid addition salt thereof.

6. The compound as defined in claim 5 which is 4-(α-phenyl-2-tolyl)-4-piperidinol or a pharmaceutically acceptable acid addition salt thereof.

7. The compound as defined in claim 1 of the formula

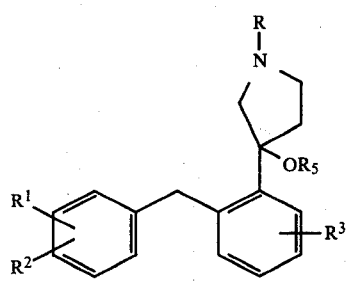

wherein
R is H, lower alkyl, cycloalkylloweralkyl, —CH₂φ, —CH₂CH₂φ, —CH₂CH₂CH₂φ, or benzoyl;
R¹ to R³ is H, —hal, 1-2C alkoxy or loweralkyl;
R⁵ is H, loweralkyl or loweracyl; or a pharmaceutically acceptable acid addition salt thereof.

8. The compound defined in claim 7 which is 3-(α-phenyl-2-tolyl)-3-pyrrolidinol or a pharmaceutically acceptable acid addition salt thereof.

9. The compound as defined in claim 1, of the formula

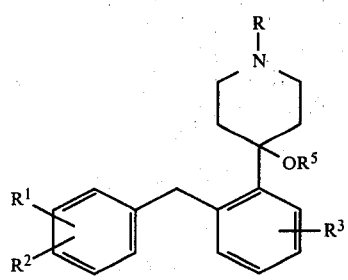

wherein
R is —H, —CH₃, —CH₂φ, —CH₂CH₂φ, or —CH₂CH₂CH₂φ;
R¹ to R³ is H, —hal, lower alkyl;
R⁵ is carboxylic acid lower acyl, benzoyl, or carboxylic acid lower cycloacyl; or a pharmaceutically acceptable acid addition salt thereof.

10. The compound as defined in claim 1 of the formula

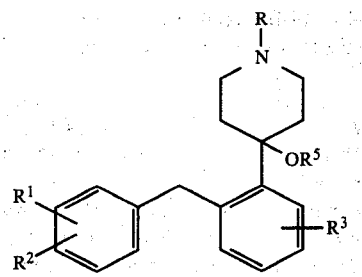

wherein R is —H or loweralkyl R⁵ is hydrogen or loweralkyl; or a pharmaceutically acceptable acid addition salt thereof.

11. A compound of the formula

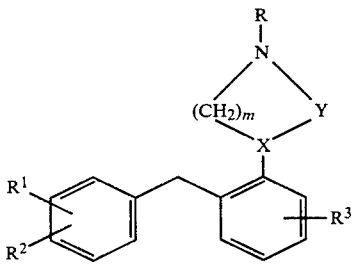

wherein X is COR⁵; Y is —(CH₂)ₙ—; R is loweralkyl, phenylloweralkyl of the formula

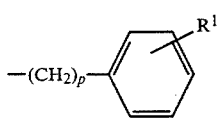

or cycloalkylloweralkyl in which the cycloalkyl portion contains from 3 to 6 carbon atoms; $R^1$, $R^2$ and $R^3$ are the same or different and each can be hydrogen, halogen, alkoxy of from 1 to 2 carbon atoms, loweralkyl, hydroxy or trifluoromethyl; $R^5$ is hydrogen, loweralkyl, carboxylic acid loweracyl, benzoyl or carboxylic acid lowercycloacyl; m is the integer 1 or 2; n is the integer 1, 2 or 3; the sum of m and n is 3 or 4; p is the integer 1, 2, 3 or 4; or a pharmaceutically acceptable acid addition salt thereof.

12. A compound as defined in claim 11 wherein R is phenylloweralkyl of the formula

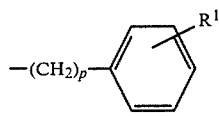

or cycloalkylloweralkyl in which the cycloalkyl portion contains from 3 to 6 carbon atoms.

13. A compound defined in claim 12 wherein X is C—OH.

14. The compound as defined in claim 11 which is 1-methyl-4-(α-phenyl-2-tolyl)-4-piperidinol or a pharmaceutically acceptable acid addition salt thereof.

15. The compound as defined in claim 11 which is 1-methyl-4-[α-(4-methoxyphenyl)-2-tolyl]-4-piperidinol or a pharmaceutically acceptable acid addition salt thereof.

16. The compound as defined in claim 11 which is 1-methyl-4-[α-(4-fluorophenyl)-2-tolyl]-4-piperidinol or a pharmaceutically acceptable acid addition salt thereof.

17. The compound defined in claim 11 which is 1-methyl-4-[α-(2-fluoro-4-methylphenyl)-2-tolyl]-4-piperidinol or a pharmaceutically acceptable acid addition salt thereof.

18. The compound defined in claim 11 which is 1-methyl-4-[α-(2,5-difluorophenyl)-2-tolyl]-4-piperidinol or a pharmaceutically acceptable acid addition salt thereof.

19. The compound defined in claim 11 which is 1-methyl-4-(α-phenyl-3-trifluoromethyl-2-tolyl)-4-piperidinol or a pharmaceutically acceptable acid addition salt thereof.

20. The compound as defined in claim 11 which is 1-(2-phenethyl-4-(α-phenyl-2-tolyl)-4-piperidinol or a pharmaceutically acceptable acid addition salt thereof.

21. The compound as defined in claim 11 which is 1-benzyl-4-[α-(2-fluoro-4-methylphenyl)-2-tolyl]-4-piperidinol or a pharmaceutically acceptable acid addition salt thereof.

22. The compound as defined in claim 11 which is 1-benzyl-4-[α-(2,5-difluorophenyl)-2-tolyl]-4-piperidinol or a pharmaceutically acceptable acid addition salt thereof.

23. The compound as defined in claim 11 which is 4-[α-(2-fluoro-4-methylphenyl)-2-tolyl]-1-phenethyl-4-piperidinol or a pharmaceutically acceptable acid addition salt thereof.

24. The compound as defined in claim 11 which is 1-benzyl-4-(α-phenyl-2-tolyl)-4-piperidinol or a pharmaceutically acceptable acid addition salt thereof.

25. The compound defined in claim 11 which is 1-n-butyl-4-(4-chloro-α-phenyl-2-tolyl)-3-pyrrolidinol or a pharmaceutically acceptable acid addition salt thereof.

26. The compound defined in claim 11 which is 3-acetoxy-1-(3-phenylpropyl)-3-(4-ethoxy-α-phenyl-2-tolyl)pyrrolidine or a pharmaceutically acceptable acid addition salt thereof.

27. The compound defined in claim 11 which is 1-benzoyl-3-(α-phenyl-2-tolyl)-3-pyrrolidinol or a pharmaceutically acceptable acid addition salt thereof.

28. The compound as defined in claim 11 which is 3-hydroxy-1-methyl-3-(α-phenyl-2-tolyl)pyrrolidine or a pharmaceutically acceptable acid addition salt thereof.

29. The compound as defined in claim 11 which is 1-benzyl-3-[α-(2,5-difluorophenyl)-2-tolyl]-3-pyrrolidinol or a pharmaceutically acceptable acid addition salt thereof.

30. The compound as defined in claim 11 which is 1-benzyl-3-(α-phenyl-2-tolyl)-3-pyrrolidinol or a pharmaceutically acceptable acid addition salt thereof.

31. The compound as defined in claim 11 which is 1-cyclopropylmethyl-3-hydroxy-3-(α-phenyl-2-tolyl)-pyrrolidine or a pharmaceutically acceptable acid addition salt thereof.

32. The compound as defined in claim 11 which is 3-acetoxy-1-benzyl-3-(α-phenyl-2-tolyl)pyrrolidine or a pharmaceutically acceptable acid addition salt thereof.

33. The compound as defined in claim 11 which is 1-benzyl-3-[α-(2-fluoro-4-methylphenyl)-2-tolyl]-3-pyrrolidinol or a pharmaceutically acceptable acid addition salt thereof.

34. The compound defined in claim 11 which is 4-acetoxy-1-methyl-4-(α-phenyl-2-tolyl)piperidine or a pharmaceutically acceptable acid addition salt thereof.

35. The compound defined in claim 11 which is 1-methyl-4-(α-phenyl-2-tolyl)-4-propionyloxypiperidine or a pharmaceutically acceptable acid addition salt thereof.

36. The compound defined in claim 11 which is 4-[α-(2-fluoro-4-methylphenyl)-2-tolyl]-4-propionyloxy-1-methylpiperidine or a pharmaceutically acceptable acid addition salt thereof.

37. The compound as defined in claim 11 which is 4-benzoyloxy-1-methyl-4-(α-phenyl-2-tolyl)piperidine or a pharmaceutically acceptable acid addition salt thereof.

38. The compound as defined in claim 11 which is 4-cyclobutylcarbonyloxy-1-methyl-4-(α-phenyl-2- tolyl)piperidine or a pharmaceutically acceptable acid addition salt thereof.

39. The compound as defined in claim 11 which is 4-cyclopropylcarbonyloxy-1-methyl-4-(α-phenyl-2-tolyl)piperidine or a pharmaceutically acceptable acid addition salt thereof.

40. The compound as defined in claim 11 which is 4-acetoxy-1-benzyl-4-(α-phenyl-2-tolyl)piperidine or a pharmaceutically acceptable acid addition salt thereof.

41. The compound as defined in claim 11 which is 4-benzoyloxy-1-(2-phenethyl)-4-(α-phenyl-2-tolyl)-piperidine or a pharmaceutically acceptable acid addition salt thereof.

42. The compound as defined in claim 11 which is 1-methyl-4-(α-phenyl-2-tolyl)-4-valeryloxypiperidine or a pharmaceutically acceptable acid addition salt thereof.

43. The compound as defined in claim 11 which is 4-methoxy-4-(α-phenyl-2-tolyl)piperidine or a pharmaceutically acceptable acid addition salt thereof.

44. The compound as defined in claim 11 which is 1-methyl-4-methoxy-4-(α-phenyl-2-tolyl)piperidine or a pharmaceutically acceptable acid addition salt thereof.

45. A method for treatment of depression which comprises administering to a depressed patient a pharmaceutically effective amount of an anti-depressant compound defined in claim 1.

46. An anti-depressant pharmaceutical composition which comprises between 0.5 and about 70 percent by weight of a compound defined in claim 11 and a pharmaceutically acceptable carrier therefor.

47. A method of tranquilizing which comprises administering to a patient in need of tranquilization an effective tranquilizing amount of a compound defined in claim 1.

48. An antidepressant pharmaceutical composition which comprises between 0.5 and about 70% by weight of a compound defined in claim 1 and a pharmaceutically acceptable carrier therefor.

49. A method for the treatment of depression which comprises administering to a depressed patient a pharmaceutically effective amount of an anti-depressor compound defined in claim 11.

50. A method of tranquilizing which comprises administering to a patient in need of tranquilization an effective tranquilizing amount of a compound defined in claim 11.

* * * * *

UNITED STATES PATENT AND TRADEMARK OFFICE
CERTIFICATE OF CORRECTION

PATENT NO. : 4,414,219

DATED : November 8, 1983

INVENTOR(S) : Lawrence L. Martin; Helen H. Ong; Vernon B. Anderson; Charles L. Crichlow It is certified that error appears in the above-identified patent and that said Letters Patent is hereby corrected as shown below:

Column 2, Line 44

"demonstrat" should be -- demonstrate --

Column 8, Line 17

"intraperitioneal" should be -- intraperitoneal --

Column 8, Line 14

"8.0" should be -- 18.0 --

Column 10, Line 67

"incude" should be -- include --

Column 12, Line 60

"combinded" should be -- combined --

Column 14, Line 54

"refrigeratio" should be -- refrigeration --

Column 17, LIne 67

"$C_{24}H_{23}NO_4$" should be -- $C_{24}H_{23}NO_2$ --

Column 20, Line 9

"30 mml" should be -- 30 ml --

UNITED STATES PATENT AND TRADEMARK OFFICE
CERTIFICATE OF CORRECTION

PATENT NO. : 4,414,219          Page 2 of 2

DATED : November 8, 1983

INVENTOR(S) : Lawrence L. Martin; Helen H. Ong; Vernon B. Anderson; Charles L. Crichlow It is certified that error appears in the above-identified patent and that said Letters Patent is hereby corrected as shown below:

Column 24, Line 63

"toyl)" should be -- tolyl) --

Column 25, Line 5

"( phenyl-2-" should be -- ( -phenyl-2- --

Column 26, Line 40

"1-cycloproylmethyl-" should be -- 1-cyclopropylmethyl- --

Column 28, Line 13

"laye" should be -- layer --

Signed and Sealed this

Twentieth Day of March 1984

[SEAL]

Attest:

GERALD J. MOSSINGHOFF

Attesting Officer      Commissioner of Patents and Trademarks